US010765637B2

(12) United States Patent
Maekawa et al.

(10) Patent No.: US 10,765,637 B2
(45) Date of Patent: Sep. 8, 2020

(54) RGD AND TRANSFERRIN NANOPARTICLE COMPOSITION

(71) Applicant: TOYO UNIVERSITY, Tokyo (JP)

(72) Inventors: Toru Maekawa, Kawagoe (JP); Sakthikumar Dasappan Nair, Kawagoe (JP); Sheikh Mohamed Mohamed, Kawagoe (JP); Srivani Veeranarayanan, Kawagoe (JP)

(73) Assignee: TOYO UNIVERSITY, Tokyo (JP)

( * ) Notice: Subject to any disclaimer, the term of this patent is extended or adjusted under 35 U.S.C. 154(b) by 0 days.

(21) Appl. No.: 16/087,557

(22) PCT Filed: Mar. 23, 2017

(86) PCT No.: PCT/JP2017/011834
§ 371 (c)(1),
(2) Date: Sep. 21, 2018

(87) PCT Pub. No.: WO2017/164331
PCT Pub. Date: Sep. 28, 2017

(65) Prior Publication Data
US 2019/0099382 A1 Apr. 4, 2019

(30) Foreign Application Priority Data
Mar. 24, 2016 (JP) ................................. 2016-060520

(51) Int. Cl.
*A61K 9/51* (2006.01)
*A61K 47/10* (2017.01)
(Continued)

(52) U.S. Cl.
CPC .............. *A61K 9/5123* (2013.01); *A61K 9/16* (2013.01); *A61K 9/5169* (2013.01);
(Continued)

(58) Field of Classification Search
CPC .. A61K 9/5123; A61K 9/5192; A61K 9/5169; A61K 9/16; A61K 38/168;
(Continued)

(56) References Cited

U.S. PATENT DOCUMENTS

2010/0076092 A1* 3/2010 Panyam ............... A61K 9/0085
514/784

FOREIGN PATENT DOCUMENTS

WO WO 2008/024753 A2 2/2008

OTHER PUBLICATIONS

Jain et al, Transferrin-Tailored solid Lipid Nanoparticles as Vectors for Site-Specific Delivery of Temozolomide to the Brain, Journal of Nanoparticle Research, vol. 15:1558, p. 1-9, ISSN:1388-0764 (Year: 2013).*

(Continued)

*Primary Examiner* — Carlos A Azpuru
(74) *Attorney, Agent, or Firm* — Birch, Stewart, Kolasch & Birch, LLP

(57) ABSTRACT

Provided is a composition which can be utilized for drug delivery systems that can penetrate the blood brain barrier, and has low cytotoxicity. A nanoparticle composition comprises nanoparticles to the surface of which a first substance and a second substance each having specificity to a tumor cell are bound, wherein the first substance having specificity to the tumor cell is a peptide comprising an amino acid sequence of arginine-glycine-aspartic acid, and wherein the second substance having specificity to the tumor cell is an iron-binding protein, and wherein the nanoparticles each comprise an outer layer and vesicles enveloped by the outer layer and the nanoparticles each comprise, as membrane components, a PEGylated phospholipid, a fatty acid with a (Continued)

melting point of 30° C. or more, and a non-PEGylated phospholipid.

17 Claims, 23 Drawing Sheets

Specification includes a Sequence Listing.

(51) Int. Cl.
| | |
|---|---|
| A61K 47/12 | (2006.01) |
| A61K 47/24 | (2006.01) |
| A61K 47/42 | (2017.01) |
| A61K 49/00 | (2006.01) |
| A61K 9/16 | (2006.01) |
| A61K 45/00 | (2006.01) |
| A61P 35/00 | (2006.01) |
| A61K 38/16 | (2006.01) |
| B82Y 5/00 | (2011.01) |

(52) U.S. Cl.
CPC .......... *A61K 9/5192* (2013.01); *A61K 38/168* (2013.01); *A61K 45/00* (2013.01); *A61K 47/10* (2013.01); *A61K 47/12* (2013.01); *A61K 47/24* (2013.01); *A61K 47/42* (2013.01); *A61K 49/00* (2013.01); *A61P 35/00* (2018.01); *A61K 49/0004* (2013.01); *B82Y 5/00* (2013.01)

(58) Field of Classification Search
CPC ........ A61K 35/00; A61K 45/00; A61K 49/00; A61K 47/10; A61K 47/12; A61K 47/24; A61K 47/42

See application file for complete search history.

(56) References Cited

OTHER PUBLICATIONS

Qin et al, Dual-Targeting Liposome Conjugated with Transferrin and Arginine-Glycine-Aspartic Acid for Glioma-Targeting Therapy, Conology Letter, vol. 8, p. 2000-2006, ISSN: 1792-1074 (Year: 2014).*

Kuo et al, Dual Targeting of Solid Lipid Nanoparticles Grafted with 83-14 MAb and anti-EGF receptor for Malignant Brain Tumor Therapy, vol. 146, p. 222-231, ISSN: 0024-3205 (Year: 2016).*
Qin et al, A Dual Targeting Liposome Conjugated With Transferrin and Arginine-Glycine-Aspartic Acid Peptide for Glioma-Targetting Therapy, Concology Letters, 8: 2000-2006 (Year: 2014).*
Mohamed, Sheikh et al, "A Dual Targeted Solid/Lipid Nanoformulation with a Plant Toxin as Therapeutic Agent for a Pragmatic Approach to Anti-Glioma Therapy", 2Nd International Symposium of Nanoparticles/Nanomaterials and Applications, Nova School of Sci and Tech, Portugal (Year: 2016).*
International Search Report for PCT/JP2017/011834 (PCT/ISA/210) dated May 23, 2017.
Jain et al., "Transferrin-tailored solid lipid nanoparticles as vectors for site-specific delivery of temozolomide to brain", Journal of Nanoparticle Research, 2013, vol. 15: 1518, pp. 1-9.
Kaur et al., "Potential of solid lipid nanoparticles in brain targeting", ScienceDirect, Journal of Controlled Release, 2008, vol. 127, pp. 97-109.
Kuo et al., "Dual targeting of solid lipid nanoparticles grafted with 83-14 MAb and anti-EGF receptor for malignant brain tumor therapy", Life Sciences, vol. 146 (2016), pp. 222-231.
Mohamed et al., "Structurally Distinct Hybrid Polymer/Lipid Nanoconstructs Harboring a Type-I Ribotoxin as Cellular Imaging and Glioblastoma-Directed Therapeutic Vectors", Macromolecular Bioscience 2014, vol. 14, pp. 1696-1711.
Qin et al., "A dual-targeting liposome conjugated with transferrin and arginine-glycine-aspartic acid peptide for glioma-targeting therapy", Oncology Letters, vol. 8, pp. 2000-2006, 2014.
Written Opinion of the International Searching Authority for PCT/JP2017/011834 (PCT/ISA/237) dated May 23, 2017.
Cheng et al., "Blood-Brain Barrier Permeable Gold Nanoparticles: An Efficient Delivery Platform for Enhanced Malignant Glioma Therapy and Imaging", Small, Dec. 29, 2014, 10 (24), pp. 5137-5150.
European Search Report for EP 17770371.7 dated Dec. 4, 2019.
Mohamed et al., "A Dual Targeted Solid/Lipid Nanoformulation with a Plant Toxin as Therapeutic Agent for a Pragmatic Approach Towards Anti-Glioma Therapy", 2nd Intl Symposium on Nanoparticles/Nanomaterials and Applications, Nova School of Sci and Tech, Portugal, Jan. 18-21, 2016.
Chinese Office Action and Search Report for Chinese Application No. 201780019637.7, dated Apr. 16, 2020.

* cited by examiner

RGD AND TRANSFERRIN NANOPARTICLE COMPOSITION

TECHNICAL FIELD

The present invention relates to a nanoparticle composition. More specifically, the present invention relates to a nanoparticle composition for delivering a drug or the like.

BACKGROUND ART

Challenges have been made to overcome barriers in delivering drugs to malignant brain tumors and treating them. Due to the complex nature and the positional problem of malignant brain tumors which are formed in brains, brain tumors have led to worldwide high mortality.

Among brain tumors, glioblastoma, which is supported by a highly organized and complex network of malignant cells, metastasizes, spreads from the primary lesion to a new area, and rapidly propagates throughout the brain. This rapid proliferation ability of glioblastoma is still present as a significant barrier for conventional treatments such as surgical tumor resection and chemotherapy.

Another main barrier limiting the success rate of chemotherapy is that almost all of the chemotherapeutic agents cannot overcome the inherent defense mechanism of the brain. It has been reported that approximately only less than 1% of chemotherapeutic agents can reach the vasculature of the central nervous system tumors via systemic administration. This is because of the presence of highly selective blood-brain barrier. Overcoming the difficulty of delivering chemotherapeutic agents to a specific region of the brain is a problem in the treatment of brain disorders.

A variety of drug delivery systems (DDS), which are capable of penetrating the blood brain barrier, have been studied. For example, Non Patent Literature 1 discloses that gold particles are used as a blood-brain-barrier-permeable drug delivery system.

Non Patent Literature 2 describes a dual-targeting liposome conjugated with transferrin and arginine-glycine-aspartic acid peptide for glioma-targeting therapy. However, Non Patent Literature 2 does not describe a liposome which comprises a fatty acid as a membrane component.

Non Patent Literature 3 describes a nanoformulation composed of a ribosome inactivating protein, curcin, and a hybrid solid-lipid nanovector for treating glioblastoma. However, Non Patent Literature 3 does not describe nanoparticles to the surface of which substances having specificity to a target cell are bound.

CITATIONS LIST

Non Patent Literatures

Non Patent Literature 1: Cheng Y., et al., Blood-brain barrier permeable gold nanoparticles: an efficient delivery platform for enhanced malignant glioma therapy and imaging, Small, 10 (24), 5137-5150, 2014.

Non Patent Literature 2: Qin L., et al., A dual-targeting liposome conjugated with transferrin and arginine-glycine-aspartic acid peptide for glioma-targeting therapy, Oncology Letters, 8, 2000-2006, 2014

Non Patent Literature 3: Mohamed M S., et al., Structurally distinct hybrid polymer/lipid nanoconstructs harboring a type-I ribotoxin as cellular imaging and glioblastoma directed therapeutic vectors. Macromolecular Bioscience, 14, 1696-1711, 2014.

SUMMARY OF INVENTION

Technical Problem

Under such circumstances, a drug delivery system is required which can penetrate the blood brain barrier, has high drug delivery efficiency and higher safety.

Accordingly, an object of the present invention is to provide a composition which can be utilized for drug delivery systems that can penetrate the blood brain barrier, and has low cytotoxicity.

Solution to Problem

The present inventors have intensively studied to solve the above problem, and consequently have found that nanoparticles to the surface of which a substance having specificity to a target cell are bound, can penetrate the blood brain barrier and be efficiently delivered into the brain (especially to the brain tumors), and completed the present invention.

The present invention includes the following aspects.

<1> A nanoparticle composition comprising nanoparticles to the surface of which a first substance and a second substance each having specificity to a tumor cell are bound, wherein the first substance having specificity to the tumor cell is a peptide comprising an amino acid sequence of arginine-glycine-aspartic acid, and wherein the second substance having specificity to the tumor cell is an iron-binding protein, and wherein the nanoparticles each comprise an outer layer and vesicles enveloped by the outer layer and the nanoparticles each comprise, as membrane components, a PEGylated phospholipid, a fatty acid with a melting point of 30° C. or more, and a non-PEGylated phospholipid.

<2> The nanoparticle composition according to <1>, wherein the fatty acid with a melting point of 30° C. or more is stearic acid, and the non-PEGylated phospholipid is phosphatidylcholine.

<3> The nanoparticle composition according to <1> or <2>, wherein the PEGylated phospholipid is phosphatidylethanolamine to which PEG is bound.

<4> The nanoparticle composition according to <3>, wherein the phosphatidylethanolamine is DSPE.

<5> The nanoparticle composition according to any one of <1> to <4>, wherein the PEGylated phospholipid has PEG which is modified with an amino group.

<6> The nanoparticle composition according to any one of <1> to <5>, wherein the nanoparticle composition comprises the first substance and the second substance at a mass ratio of 2:8 to 8:2.

<7> The nanoparticle composition according to any one of <1> to <6>, wherein the nanoparticle further comprises a drug.

<8> The nanoparticle composition according to <7>, wherein the drug is an anti-cancer agent.

<9> The nanoparticle composition according to any one of <1> to <8>, wherein the nanoparticle further comprises an imaging agent.

<10> A method for producing a nanoparticle composition comprising nanoparticles to the surface of which a first substance and a second substance each having specificity to a tumor cell are bound, comprising:

(i) removing a volatile organic solvent from a solution comprising a PEGylated phospholipid, a fatty acid with a melting point of 30° C. or more, and a non-PEGylated phospholipid in the volatile organic solvent to form a membrane, (ii) sonicating the membrane formed in the step (i) in a buffer to produce a nanoparticle, and (iii) binding the first substance and the second substance each having specificity to the tumor cell to the surface of the nanoparticles produced in the step (ii), wherein the first substance having specificity to the tumor cell is a peptide comprising an amino acid sequence of arginine-glycine-aspartic acid, and wherein the second substance having specificity to the tumor cell is an iron-binding protein.

<11> The method according to <10>, wherein in the step (ii), the buffer comprises a drug, and nanoparticles comprising the drug are produced.

<12> The method according to <11>, wherein the drug is an anti-cancer agent.

<13> The method according to any one of <10> to <12>, further comprising introducing an imaging agent into the nanoparticle.

<14> A pharmaceutical composition for treating cancer, comprising the nanoparticle composition according to <8>.

<15> The pharmaceutical composition according to <14>, wherein the cancer is a brain tumor.

<16> A method for treating cancer, comprising administering the pharmaceutical composition according to <14> or <15> to a subject having cancer.

<17> The method according to <16>, wherein the cancer is a brain tumor.

<18> A composition for imaging a tumor cell, comprising the nanoparticle composition according to <9>.

<19> A method for detecting a brain tumor, comprising administering the composition according to <18> to a subject in need thereof and detecting a localization of the imaging agent in a brain.

<20> A method for monitoring the effect of a therapy against a brain tumor, comprising administering the composition according to <18> to a subject in need thereof and detecting a localization of the imaging agent in a brain.

The invention further includes the following aspects.

<101> A composition comprising a compound represented by the following formula (1), a fatty acid with a melting point of 30° C. or more, and a phospholipid:

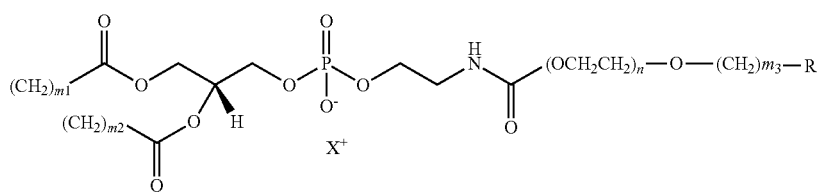

(1)

(wherein m1 and m2 each independently represent an integer of 10 to 25, n represents an integer of 20 to 60, m3 represents an integer of 0 to 10, R represents a group comprising a carboxy, amino or amide group, and $X^+$ represents a cation.).

<102> The composition according to <101>, which further comprises a drug.

<103> The composition according to <102>, wherein the drug is curcin.

<104> The composition according to any one of <101> to <103>, wherein, regarding the compound represented by formula (1), R in the formula (1) comprises a first substance having specificity to a target cell.

<105> The composition according to any one of <101> to <104>, wherein, regarding the compound represented by formula (1), R in the formula (1) comprises a second substance having specificity to a target cell.

<106> The composition according to <104> or <105>, wherein the first substance having specificity to the target cell is a peptide having an amino acid sequence of arginine-glycine-aspartic acid.

<107> The composition according to <105> or <106>, wherein the second substance having specificity to the target cell is transferrin.

<108> The composition according to any one of <101> to <107>, wherein the composition is in the form of a particle having a diameter of 500 nm or less.

<109> A composition according to any one of <102> to <108>, wherein the composition is for treating a brain tumor.

The invention further includes the following aspects.

<1001> A nanoparticle composition comprising nanoparticles to the surface of which a first substance and a second substance each having specificity to a tumor cell are bound, wherein the first substance having specificity to the tumor cell is a peptide comprising an amino acid sequence of arginine-glycine-aspartic acid, and wherein the second substance having specificity to the tumor cell is an iron-binding protein, and wherein the nanoparticles each comprise an outer layer and vesicles enveloped by the outer layer and the nanoparticles each comprise, as membrane components, a PEGylated phospholipid, a fatty acid with a melting point of 30° C. or more, and a non-PEGylated phospholipid.

<1002> The nanoparticle composition according to <1001>, wherein the PEGylated phospholipid is DSPE-PEG (2000) amine, wherein the fatty acid is stearic acid, and wherein the non-PEGylated phospholipid is phosphatidylcholine.

<1003> The nanoparticle composition according to <1001> or <1002>, wherein the nanoparticle composition comprises the first substance and the second substance at a mass ratio of 2:8 to 8:2.

<1004> The nanoparticle composition according to any one of <1001> to <1003>, wherein the nanoparticle further comprises a drug.

<1005> The nanoparticle composition according to <1004>, wherein the nanoparticle further comprises an imaging agent.

<1006> The nanoparticle composition according to any one of <1001> to <1003>, wherein the nanoparticle further comprises an imaging agent.

<1007> The nanoparticle composition according to <1004>, wherein the drug is an anti-cancer agent.

<1008> A method for producing a nanoparticle composition comprising nanoparticles to the surface of which a first substance and a second substance each having specificity to a tumor cell are bound, comprising:

(i) removing a volatile organic solvent from a solution comprising a PEGylated phospholipid, a fatty acid with a melting point of 30° C. or more, and a non-PEGylated phospholipid in the volatile organic solvent to form a membrane, (ii) sonicating the membrane obtained in the step (i) in a buffer to produce nanoparticles, and (iii) binding the first substance and the second substance each having specificity to the tumor cell to the surface of the nanoparticles obtained in the step (ii), wherein the first substance having specificity to the tumor cell is a peptide comprising an amino acid sequence of arginine-glycine-aspartic acid, and wherein the second substance having specificity to the tumor cell is an iron-binding protein.

<1009> The method according to <1008>, wherein in the step (ii), the buffer comprises a drug, and nanoparticles comprising the drug are produced.

<1010> The method according to <1009>, further comprising introducing an imaging agent into the nanoparticle.

<1011> A nanoparticle composition produced by the method according to <1009> or <1010>.

<1012> The method according to <1009>, wherein the drug is an anti-cancer agent.

<1013> A nanoparticle composition produced by the method according to <1012>.

<1014> The method according to <1008>, further comprising introducing an imaging agent into the nanoparticle.

<1015> A nanoparticle composition produced by the method according to <1014>.

<1016> The pharmaceutical composition for treating cancer, comprising the nanoparticle composition according to <1007> or <1013>.

<1017> The pharmaceutical composition according to <1016>, wherein the cancer is a brain tumor.

<1018> A method for treating cancer, comprising administering the pharmaceutical composition according to <1016> or <1017> to a subject having cancer.

<1019> The method according to <1018>, wherein the cancer is a brain tumor.

<1020> A composition for imaging a tumor cell, comprising the nanoparticle composition according to <1006> or <1015>.

<1021> A method for detecting a brain tumor, comprising administering the composition according to <1020> to a subject in need thereof and detecting a localization of the imaging agent in a brain.

<1022> A method for monitoring the effect of a therapy against a brain tumor, comprising administering the composition according to <1020> to a subject in need thereof and detecting a localization of the imaging agent in a brain.

This description includes the disclosure of Japanese Patent Application No. 2016-060520, of which this application claims the priority.

Advantageous Effects of Invention

According to the present invention, there is provided a composition which can be utilized for drug delivery systems that can penetrate the blood brain barrier, and has low cytotoxicity.

DESCRIPTION OF EMBODIMENTS

[Nanoparticle Composition]

Figure 1:
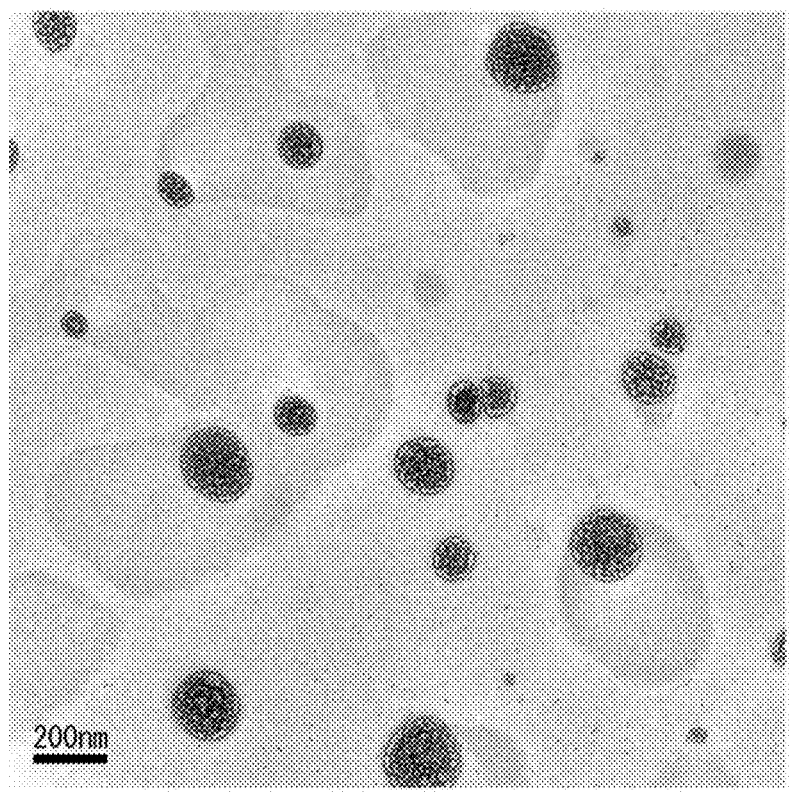
FIG. 1 is a photograph of a typical transmission electron microscope image of nanoparticles according to one embodiment.

The present invention relates to a nanoparticle composition. As used herein, "nanoparticle" means a particle having the diameter of approximately no more than 1 μm (preferably, of 1 nm or more and less than 1 μm). In the present invention, the nanoparticles are each formed of a membrane comprising a lipid as a major component, and may comprise an outer layer and vesicles enveloped by the outer layer.

In one embodiment, the nanoparticles may comprise a PEGylated phospholipid, a fatty acid with a melting point of 30° C. or more, and a non-PEGylated phospholipid as membrane components (membrane components of the outer layer and the vesicles). The nanoparticles may comprise other components. In the present invention, the nanoparticles may not comprise cholesterol as a membrane component.

As used herein, "PEGylated phospholipid" refers to a phospholipid to which polyethylene glycol (PEG) is bound. Examples of the PEGylated phospholipid include, but are not limited to, phosphatidylethanolamine to which PEG is bound (i.e., 1,2-diacyl-sn-glycero-3-phosphoethanolamine). PEG may be bound to an amino group in the phosphatidylethanolamine. Two fatty acids in the phosphatidylethanolamine may each independently represent a saturated fatty acid having 10 to 25 or 16 to 20 carbon atoms. PEG may be mPEG (methoxy PEG). Phosphatidylethanolamine may be, for example, DSPE (1,2-di stearoyl-sn-glycero-3-phosphoethanolamine), DPPE (1,2-dipalmitoyl-sn-glycero-3-phosphoethanolamine) or DMPE (1,2-myristoyl-sn-glycero-3-phosphoethanolamine).

A polyethylene glycol (PEG) chain in the PEGylated phospholipid may have an average molecular weight (Mw) of 500 to 10,000, preferably 1,000 to 5,000, or 1,000 to 3,000, for example, of 2,000.

The PEGylated phospholipid may be modified with a functional group, especially at the free end of the PEG chain. The functional group may be, for example, an amino group, a carboxy group, or an amide group. The PEGylated phospholipid modified with an amino group may be 1,2-distearoyl-sn-glycero-3-phosphoethanolamine-N-[amino(polyethylene glycol)-2000], which is, for example, available from Avanti Polar Lipids, Inc. as DSPE-PEG(2000) Amine. The PEGylated phospholipid modified with a carboxy group may be 1,2-distearoyl-sn-glycero-3-phosphoethanolamine-N-[carboxy(polyethylene glycol)-2000], which is, for example, available from Avanti Polar Lipids, Inc. as DSPE-PEG(2000) Carboxylic acid.

In one embodiment, a compound represented by formula (1) may be used as the PEGylated phospholipid to prepare a nanoparticle composition.

In formula (1), m1 and m2 each independently represent an integer of 10 to 25, n represents an integer of 20 to 60, m3 represents an integer of 0 to 10, R represents a group comprising a carboxy, amino or amide group, and $X^+$ represents a cation.

It is preferred that m1 and m2 in the formula (1) each independently represent a number corresponding to the number of carbon atoms in the fatty acid which is solid at room temperature, and may be, for example, 15 to 25, for instance, 15 to 20, or 16 to 18, specifically 17. Further, n in the formula (1) may be, for example, 25 to 55, or, for instance, 30 to 50.

Further, m3 in the formula (1) is an integer of 0 to 10, for example, 0 to 6, or, for example, 0, 1 or 2.

$X^+$ in the formula (1) is a cation, and examples of the cation include an ammonium cation, a sulfonium cation, an iodonium cation, a phosphonium cation, and a hydrogen ion.

By using a carboxy group or amino group of R in the formula (1), the substance having specificity to a target cell in the drug delivery can be bound to the nanoparticles via, for example, an amide bond, which allows the nanoparticles to accumulate in the target cell. The substance can also be bound to the nanoparticles via a covalent bond by cross-linking reaction or the like using a chemical crosslinking agent.

As used herein, "fatty acid with a melting point of 30° C. or more" may include a fatty acid which is solid at room temperature. For example, the fatty acid with a melting point of 30° C. or more may be one or more fatty acids selected from saturated fatty acids having 10 to 25 carbon atoms, and more specifically, may be, for example, capric acid, lauric acid, myristic acid, pentadecanoic acid, palmitic acid, heptadecanoic acid, stearic acid, arachidic acid, behenic acid, or lignoceric acid.

Further, as used herein, "non-PEGylated phospholipid" may include glycerophospholipids such as phosphatidyl glycerides such as lecithin (phosphatidylcholine), phosphatidylserine, phosphatidylglycerol, phosphatidylethanolamine and phosphatidylinositol, and sphingophospholipids such as sphingomyelin. In one embodiment, the non-PEGylated phospholipid may be one or more phosphatidyl glycerides selected from the group consisting of phosphatidylcholine, phosphatidylserine, phosphatidylglycerol, phosphatidylethanolamine and phosphatidylinositol.

The nanoparticles each comprising a fatty acid with a melting point of 30° C. or more and a phospholipid as membrane components has an advantage of high stability.

Since the PEGylated phospholipid (for example, a compound represented by formula (1) described above) has a lipid moiety and a polymer moiety, the nanoparticles according to the present invention are a hybrid of a solid-lipid nanoparticle and a polymeric particle. The solid-lipid nanoparticle is a solid lipid particle in which the lipid core is solid

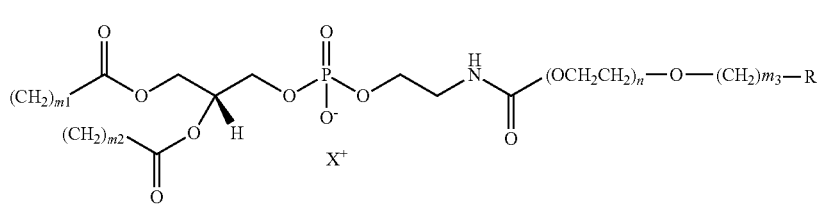

(1)

at room temperature. The nanoparticles according to the present invention can also be referred to as a hybrid solid-lipid nanoparticle.

The mass ratio of the PEGylated phospholipid, the fatty acid with a melting point of 30° C. or more, and the non-PEGylated phospholipid comprised as membrane components in the nanoparticles is not particularly limited as long as the nanoparticles are formed, and may be, for example, (1 to 10):(1 to 10):(1 to 10). The molar ratio of the total of PEGylated phospholipid and non-PEGylated phospholipid to the fatty acid with a melting point of 30° C. or more comprised as membrane components in the nanoparticles may be, for example, 1:1 to 1:5, 1:1.3 to 1:4, or 1:1.5 to 1:3. The molar ratio of the PEGylated phospholipid to the fatty acid with a melting point of 30° C. or more comprised as membrane components in the nanoparticles may be 1:50 to 1:3, 1:30 to 1:5, 1:20 to 1:6, or 1:15 to 1:8.

The average diameter of the nanoparticles comprised in the composition of the present embodiment may be 500 nm or less, 400 nm or less, 300 nm or less, or 200 nm or less. The average diameter of the nanoparticles may be more than 130 nm or more, 140 nm or more, 150 nm or more, 160 nm or more, 170 nm or more, 180 nm or more, or 190 nm or more. The average diameter of the nanoparticle, for example, may be in the range of 140 to 500 nm, 150 to 300 nm, or 160 to 200 nm. The diameter of the particle can be measured by methods known in the art, in particular, by the dynamic light scattering method. Measurement by the dynamic light scattering method can be carried out using a commercially available analyzer, such as Zetasizer Nano-ZS (Malvern Instruments Ltd.). Further, the diameter of the particle may be measured, for example, by measuring the diameter in the transmission electron microscope image of the particle. If the image of the particle is not circular, the diameter of a circle having the same area as the image of the particle can be defined as the diameter of the particle. The nanoparticles according to the invention each may comprise an outer layer and vesicles enveloped by the outer layer, in which the diameter of the outer layer is defined as the diameter of the particle. The diameter of the particle may be an average value (for example, in the case of measuring the diameter with the transmission electron microscope image, the diameter of the particle may be the average value of measured diameters of 100 particles).

It is preferred that the nanoparticles in this invention are not aggregated. Further, it is preferred that the nanoparticles have a negative zeta potential. The zeta potential of the nanoparticles may be, more preferably, for example, −100 mV to −1 mV, −80 mV to −2 mV or −50 mV to −3 mV, or −30 mV to −5 mV. Negative zeta potential indicates that the particle is hydrophilic. The zeta potential of the particle can be measured by an electrophoretic light scattering method. Measurement of zeta potential by the electrophoretic light scattering method can be performed by methods known in the art, for example, using a commercially available analyzer, such as Zetasizer Nano-ZS (Malvern Instruments Ltd.).

The conventional method for manufacturing a solid-lipid nanoparticle may comprise an emulsion-dispersion process which requires the use of surfactants. The use of surfactants may lead to increase in cost, and the emulsion-dispersion process tends to be complicated and time consuming. Further the obtained solid-lipid nanoparticle is low in loading of drugs and can cause leakage of drugs.

In contrast, as described later in Examples, the present invention can form nanoparticles being high in loading of drugs and maintaining drug release for a long time. This indicates that the drug is encapsulated by a dual membrane of polymer and lipid, the drug is not released until the drug pass through the lipid/polymer layer, and as a result, the sustained and delayed drug release can be achieved.

Further, the nanoparticles according to the present invention each may comprise an outer layer and vesicles enveloped by the outer layer, for example, as shown in FIG. 1. Such a structure allows the contained drug to be released for a long time.

In the present invention, a substance having specificity to a target cell may be bound to the surface of the nanoparticles. As used herein, "substance having specificity to a target cell" refers to a substance having a property of more easily binding to the target cell compared to other cells. The substance having specificity to a target cell may be bound to at least some molecules of PEGylated phospholipids (especially to a functional group modifying the PEG chain) comprised as a membrane component in the nanoparticles. The binding may be preferably via a covalent bond. The binding may be performed by techniques known in the art. For example, the binding is via an amide bond between the amino group bound to a PEGylated phospholipid and the carboxy group of the substance having specificity to a target cell.

The target cell may be a brain cell. The target cell may be a tumor cell, especially a glioblastoma cell.

In one embodiment, a first substance and a second substance each having specificity to a target cell may be bound to the surface of the nanoparticle, wherein the second substance is a different substance from the first substance. In this case, the composition of this embodiment has dual target signals, so that the nanoparticles more efficiently accumulate in the target cell.

In one embodiment, a substance having specificity to a target cell may be bound to at least some molecules of the compound represented by formula (1) described above. More specifically, some molecules of the compounds represented by formula (1) may be a compound in which R in the formula (1) is a first substance having specificity to a target cell. In such a case, R comprises an amide group so that the first substance having specificity to a target cell is bound via an amide bond.

Further, the substance having specificity to a target cell may include a second substance which is different from the first substance.

The substance having specificity to a target cell is not particularly limited, and any material can be used as the substance depending on the target cell. The substance having specificity to a target cell includes, for example, an antibody, antibody fragment or aptamer against a protein present on the surface of the target cell; or a ligand for a receptor present on the surface of target cell.

Examples of the substance having specificity to a target cell include a peptide having an amino acid sequence (RGD sequence) of arginine-glycine-aspartic acid (RGD), which binds to integrin present on the surface of cells. A peptide having RGD sequence has specificity especially for vascular endothelial cancer cells.

As the peptide having RGD sequence, a peptide comprising RGD sequence can be used. As used herein, "peptide" refers to an amino acid polymer in which two or more amino acids are bound via a peptide bond. The number of amino acids included in the peptide is not particularly limited, but may be, for example, 2 to 100, or 3 to 50. The peptide having RGD sequence may be 3 to 10, for example, 3, 4, 5 or 6 amino acid residues in length. Examples of the peptide having RGD sequence include RGD tripeptide, a pentapeptide having the amino acid sequence of GRGDS (SEQ ID NO: 1), a hexapeptide having the amino acid sequence of GRGDNP (SEQ ID NO: 2), and disintegrins or the like. The peptide having RGD sequence may be prepared, for example, by chemical synthesis using a commercially available peptide synthesizer, or may be prepared by genetic engineering techniques. Alternatively, a commercially available peptide having RGD sequence, such as the one available from Sigma-Aldrich Co. LLC., may be used.

Other examples of the substance having specificity to a target cell include an iron-binding protein. The iron-binding protein refers to any protein that has a property of binding to iron. Examples of the iron-binding protein include, but are not limited to, transferrin, lactoferrin, and ovotransferrin, and variants/mutants thereof. The variant/mutant may include a variant having substitution, deletion and/or insertion of amino acid(s) (for example, 1 to 10 amino acids) in a naturally occurring protein. The variant/mutant can retain specificity to the target cell. The iron-binding protein is preferably transferrin, which is a ligand for transferrin receptors present a lot on the surface of cancer cells. Transferrin is a protein of about 79 kDa. The iron-binding protein is not particularly limited to, and may be derived from mammals such as human and cattle. The iron-binding protein may be prepared by methods known in the art, for example, by using genetic engineering techniques. Alternatively, a commercially available iron-binding protein, such as the one available from Sigma-Aldrich Co. LLC., may be used.

As described later in Examples, the nanoparticles to which both RGD tripeptides and transferrin are bound were capable of passing through a blood brain barrier and delivering drugs very efficiently to brain tumors. Thus, the nanoparticle composition of the present embodiment can also be considered to be for treating a brain tumor.

Further, other examples of the substance having specificity to a target cell include folic acid, low density lipoprotein, amino glucose, and epidermal growth factor.

The nanoparticle composition comprising nanoparticles to the surface of which a first substance and a second substance each having specificity to a target cell are bound may comprise the first substance and the second substance at any ratio. For example, when the first substance having specificity to a target cell is a peptide having RGD sequence, and the second substance having specificity to a target cell is an iron-binding protein, the nanoparticle composition may comprise the first substance and the second substance at a mass ratio of 1:20 to 20:1, 1:10 to 10:1, 2:8 to 8:2, 3:7 to 7:3, or 4:6 to 6:4, more specifically at a mass ratio of 35:65 to 45:55. When the first substance having specificity to a target cell is a peptide having RGD sequence and the second substance having specificity to a target cell is an iron-binding protein, the nanoparticle composition may comprise the first substance and the second substance at a molar ratio of 10:1 to 2,000:1, 50:1 to 1,000:1, 80:1 to 500:1, 100:1 to 400:1, 120:1 to 300:1, or 130:1 to 200:1. The first and second substances may be bound to the surface of nanoparticle at these mass ratios or molar ratios.

In one embodiment, the nanoparticle may further comprise a drug. The nanoparticle comprising a drug can be applied for drug delivery systems. The drug, depending on the nature, may be encapsulated by the membrane of the nanoparticles or may be incorporated among the membrane components.

Examples of the drug include an anti-cancer agent, but the drug is not particularly limited to, and various drugs with different properties and activities can be used in the present invention. Examples of the anti-cancer agent include, but are not particularly limited to, DNA synthesis inhibitors such as fluorouracil, azathioprine and methotrexate; antimitotic agents such as irinotecan, vinblastine and paclitaxel; DNA damaging agents such as cisplatin and nitrogen mustard; antitumor antibiotics such as doxorubicin, and bleomycin; and compounds having cell killing activity, such as curcin. Curcin is a toxic protein (type I ribosome-inactivating glycoprotein being hydrophobic and having a molecular weight of 28 kDa) comprised in seeds of *Jatropha curcas*, which is one kind of plant, and is known to have a potent killing activity against cancer cells. The drug may be a nucleic acid, a protein, a peptide, or a small molecule compound (e.g., a compound having a molecular weight of 1,000 or less), and the like. The molecular weight of the drug may be, but is not limited to, 200 Da to 50 kDa or 400 Da to 30 kDa. For example, the drug may be a protein having a molecular weight of 10 kDa to 40 kDa or 20 kDa to 30 kDa. The drug may be a taxane compound (for example, paclitaxel or docetaxel) or an anthracycline compound (for example, doxorubicin, pirarubicin, idarubicin, aclarubicin, daunorubicin, epirubicin, amrubicin, or mitoxantrone). The drug may be hydrophilic or hydrophobic.

These drugs may be used alone or in combination of two or more. As used herein, "compound" may include not only a compound in the free form, but also a salt and a hydrate thereof, and the like.

The nanoparticle comprising a drug according to the present invention can be delivered efficiently to tumors, particularly to brain tumors, have high stability, and release a drug for a long time.

In one embodiment, the nanoparticle may further comprise an imaging agent. The nanoparticle comprising an imaging agent may be applied for imaging a target cell. In one embodiment, the imaging of tumors enables, for example, detection and diagnosis of tumors as well as monitoring of the effect of a therapy against tumors. The imaging agent, depending on the nature, may be contained in the aqueous phase encapsulated by the membrane of the nanoparticles or may be incorporated among the membrane components. The imaging agent may be bound to the surface of nanoparticle. The nanoparticles may comprise both of the drug and the imaging agent.

Examples of the imaging agent include a fluorescent substance, a light-emitting substance, a quantum dot, a radioactive substance, an MRI contrast agent, an X-ray contrast agent, and a paramagnetic ion.

The nanoparticle comprising an imaging agent of the present invention may be delivered efficiently to tumors, in particular to brain tumors, and may be used in imaging of tumors.

The nanoparticle composition of the present embodiment may be produced by any method known in the art, but in particular, can be produced according to the section "Method for Producing Nanoparticle Composition" described below.

The nanoparticles according to the present invention, for example as shown in FIG. 1, each may comprise an outer layer and vesicles enveloped by the outer layer. Such a structure allows a drug contained in the particle to be released for a long time. Further, the nanoparticles according to the present invention have the advantage of high stability and excellent dispersibility. The nanoparticles to the surface of which substances having specificity to a target cell (especially a brain tumor cell) are bound can pass through the blood brain barrier and deliver a drug or an imaging agent to brain tumors with high specificity, and has an advantage of low accumulation in non-specific tissues. Further, the nanoparticles according to the present invention circulate in blood for a long time, thereby enabling the long-term delivery to the target cell.

[Method for Producing Nanoparticle Composition]

The present invention provides a method for producing a nanoparticle composition according to the present invention. This method may comprise (i) removing a volatile organic solvent from a solution comprising a PEGylated phospholipid, a fatty acid with a melting point of 30° C. or more, and a non-PEGylated phospholipid in the volatile organic solvent to form a membrane, and (ii) sonicating the membrane obtained in the step (i) in a buffer to produce nanoparticles (non-targeted nanoparticles). The method may further comprise (iii) binding substances having specificity to the target cell to the surface of the nanoparticles (non-targeted nanoparticles). The method may further comprise introducing a drug or an imaging agent into the nanoparticle. As used herein, "non-targeted nanoparticles" refers to nanoparticles to the surface of which no substance having specificity to a target cell is bound.

In the step (i) of the method, the solution comprising a PEGylated phospholipid, a fatty acid with a melting point of 30° C. or more, and a non-PEGylated phospholipid can be prepared, for example, by dissolving these substances in a common volatile organic solvent in the art, such as chloroform, toluene, ethanol, acetone, methanol, or dimethyl sulfoxide. The method may comprise the step of preparing a solution comprising a PEGylated phospholipid, a fatty acid with a melting point of 30° C. or more, and a non-PEGylated phospholipid in a volatile organic solvent. The mass ratio of the PEGylated phospholipid, the fatty acid with a melting point of 30° C. or more, and the non-PEGylated phospholipid in the solution is not particularly limited as long as the nanoparticles are formed, and may be, for example, (1 to 10):(1 to 10):(1 to 10). The concentrations of the PEGylated phospholipid, the fatty acid with a melting point of 30° C. or more, and the non-PEGylated phospholipid in a solution, may be, for example, 0.1 to 200 mg/mL, 1 to 100 mg/mL, and 10 to 50 mg/mL, respectively. The molar ratio of the total of PEGylated phospholipid and non-PEGylated phospholipid to the fatty acid with a melting point of 30° C. or more in a solution, may be, for example, 1:1 to 1:5, 1:1.3 to 1:4, or 1:1.5 to 1:3. The molar ratio of the PEGylated phospholipid to the fatty acid with a melting point of 30° C. or more in a solution may be 1:50 to 1:3, 1:30 to 1:5, 1:20 to 1:6, or 1:15 to 1:8.

In one embodiment, the solution comprising a PEGylated phospholipid, a fatty acid with a melting point of 30° C. or more, and a non-PEGylated phospholipid may further comprise a drug or an imaging agent. Thus, the produced nanoparticle can comprise the drug or the imaging agent within the membrane.

In the step (i) of the method, a volatile organic solvent is removed from the solution comprising the PEGylated phospholipid, the fatty acid with a melting point of 30° C. or more, and the non-PEGylated phospholipid in the volatile organic solvent, thereby a membrane being formed. The volatile organic solvent may be removed by methods known in the art, for example, by vacuum drying.

Then, in the step (ii) of the method, the membrane obtained in the step (i) is sonicated in a buffer to produce nanoparticles. The buffer may be a physiological buffer, for example, phosphate buffered saline (PBS). The pH of the buffer may be, but is not limited to, for example, 6.8 to 8.0, 7.0 to 7.8, or 7.2 to 7.6. In one embodiment, the buffer may further comprise a drug or an imaging agent. Thus, the produced nanoparticle can contain the drug or the imaging agent encapsulated by the membrane. The concentration of the drug or the imaging agent in the buffer, can be modulated by those skilled in the art appropriately according to any purpose, and may be, for example, 0.01 mg/mL to 100 mg/mL, 0.1 mg/mL to 20 mg/mL, or 1 mg/mL to 10 mg/mL. Sonication can be carried out by methods known in the art, for example, by using a commercially available sonicator. Sonication may be carried out until a clear, stable suspension is obtained. Sonication may be carried out, for example, at a frequency of 10 to 200 kHz or 20 to 100 kHz.

The produced nanoparticle may be pelleted for purification, for example, by performing centrifugation (e.g. centrifugation at 30,000 to 70,000 rpm for 20 minutes to 1 hour). Centrifugation may be performed a plurality of times.

Then, in the step (iii) of the method, a substance having specificity to a target cell can be bound to the surface of the nanoparticles obtained in the step (ii) (non-targeted nanoparticle). Binding can be performed by any technique known in the art, but particularly may be carried out using a chemical crosslinking agent. Examples of the chemical crosslinking agent include 1-ethyl-3-[3-dimethylaminopropyl]carbodiimide hydrochloride (EDC) and N-hydroxysuccinimide (NHS). In one embodiment, the substance having specificity to a target cell can be bound to the surface of the nanoparticles by activating the substance having specificity to a target cell with a chemical crosslinking agent, and reacting the activated substance with the nanoparticles obtained in the step (ii) (in particular, with an amino group bound to the PEGylated phospholipid in membrane components of the nanoparticles). The reaction conditions between the activated substance having specificity to a target cell and the nanoparticles can be appropriately set by those skilled in the art, but may be, for example, at 0 to 10° C. for 3 to 24 hours. The amount of the substance having specificity to a target cell (the total amount of the substances in the case of two or more substances) may be, for example, 5 to 40% (by mass) or 10 to 30% (by mass) relative to the amount of nanoparticles being a reaction counterpart.

When PEGylated phospholipid is a compound represented by formula (1) described above, the substance having specificity to a target cell may be bound to R in the formula (1).

When two or more substances having specificity to a target cell are to be bound, the bindings of two or more substances to the nanoparticles can be caused separately or simultaneously. Simultaneous binding of the two or more substances to the nanoparticles can make the production of the nanoparticles simpler.

The nanoparticles to the surface of which substances having specificity to a target cell are bound may be pelleted for purification, for example, by performing centrifugation (e.g. centrifugation at 30,000 to 70,000 rpm for 20 minutes to 1 hour). Centrifugation may be performed a plurality of times.

In one embodiment, the invention provides a nanoparticle composition produced by the method described above.

[Methods of Treating and Imaging Brain Tumor]

The present invention provides a pharmaceutical composition for treating cancer, comprising the nanoparticles comprising an anti-cancer agent according to an embodiment of the present invention. The cancer is preferably a brain tumor.

As used herein, "brain tumor" refers to any tumor occurring in the cranium. Examples of the brain tumor include, but are not limited to, glioma, astrocytoma, oligodendroglioma, anaplastic astrocytoma, anaplastic oligodendroglioma, and glioblastoma. Glioblastoma is the highest grade glioma.

As used herein, "treatment" or "treating" means causing shrinkage or disappearance of a brain tumor in a subject having the brain tumor. The subject having a brain tumor can be determined, for example, by diagnostic imaging such as CT (computed tomography) and MRI (magnetic resonance imaging).

The pharmaceutical composition may further comprise any formulation auxiliary usually used in the pharmaceutical field. As used herein, "formulation auxiliary" may include various pharmaceutically acceptable carriers or additives, such as carriers (solid or liquid carriers), excipients, stabilizers, disintegrators, surfactants, binders, lubricants, emulsifiers, antioxidants, odor-improving agents, fillers, dissolution adjuvants, suspending agents, coating agents, colorants, flavoring agents, preservatives and buffers. Specific examples of the formulation auxiliary include water, saline, other aqueous solvents, pharmaceutically acceptable organic solvents, mannitol, lactose, starch, microcrystalline cellulose, dextrose, calcium, polyvinyl alcohol, collagen, polyvinyl pyrrolidone, carboxyvinyl polymer, sodium alginate, water-soluble dextran, water-soluble dextrin, sodium carboxymethyl starch, pectin, gum arabic, xanthan gum, casein, gelatin, agar, propylene glycol, polyethylene glycol, vaseline, paraffin, glycerin, stearyl alcohol, stearic acid, and sorbitol. The formulation auxiliary may be selected appropriately or in combination, depending on the dosage form of the preparation.

The pharmaceutical composition can be administered orally or parenterally, e.g., intravenously, to a subject. The pharmaceutical composition may be formulated in oral dosage forms such as tablets, pills, capsules, granules, powdered medicines, powders, and liquids, or in parenteral dosage forms such as injections, drops, or liniments. A person skilled in the art can produce these preparations by conventional methods.

The pharmaceutical composition can be administered at a therapeutically effective amount. Specific doses of pharmaceutical composition are determined depending on progression or severity of disease, general health status, age, gender, bodyweight, tolerance for treatment or the like of individual subjects, for example, by the decision of the physician. For example, a pharmaceutical composition may be administered at a dose of anti-cancer agents, in nanoparticles, of 0.000001 mg/kg body weight/day to 1,000 mg/kg body weight/day, or 0.001 mg/kg body weight/day to 1 mg/kg body weight/day, or 0.005 mg/kg body weight/day to 0.5 mg/kg body weight/day, or 0.01 mg/kg body weight/day to 0.1 mg/kg body weight/day. A pharmaceutical composition can be administered at a single dose or multiple doses, for example, may be administered to a subject a couple of times or dozens of times with a given dosing interval, for example, at an interval of one, two, three, four, five, or six days, or one, two, or three weeks, or one month or the like.

The pharmaceutical compositions may be used in combination with other anti-cancer agent treatment, surgery (surgical treatment), or radiation treatment.

The subject to which the pharmaceutical composition is administered may be mammals, such as primates, various livestock, poultry, pets, and experimental animals, and preferably human. The subject may be a subject having cancer, preferably a subject having a brain tumor.

The present invention further provides a method for treating cancer, comprising administering the nanoparticles or pharmaceutical composition comprising an anti-cancer agent according to an embodiment of the present invention to a subject having cancer. The cancer may be a brain tumor.

The present invention further provides use of nanoparticles according to an embodiment of the present invention, for the manufacture of a cancer therapeutic agent.

The administration of the pharmaceutical composition can also extend survival periods of a subject having cancer, especially of a subject having a brain tumor, compared to subjects not receiving the administration.

The present invention also provides a composition for imaging a tumor cell, comprising the nanoparticles comprising an imaging agent according to an embodiment of the present invention. The composition may further comprise a formulation auxiliary described above. The administration route, dosage form, dose, the number of administration and dosing interval of the present composition may be appropriately set according to those described above or those known in the art with respect to pharmaceutical compositions.

The present invention also provides a method for detecting a brain tumor, comprising administering the nanoparticles or composition comprising an imaging agent according to an embodiment of the present invention to a subject in need thereof, and detecting a localization of the imaging agent in a brain. The subject may be a subject having a brain tumor or a subject suspected of having a brain tumor. The method may further comprise detecting or diagnosing a brain tumor, and then treating the brain tumor.

The present invention further provides a method for monitoring an effect of a therapy against a brain tumor, comprising administering the nanoparticles or composition comprising an imaging agent according to an embodiment of the present invention to a subject in need thereof, and detecting a localization of the imaging agent in a brain. The subject may have received a therapy against brain tumors. The administration and detection in the method may be usually performed a plurality of times with appropriate time intervals.

EXAMPLES

Next, the present invention is described in detail by referring to Examples, but the present invention is not limited the following Examples.

[Materials and Methods]
(Analysis of Nanoparticles)

The morphology of nanoparticles was observed by a transmission electron microscope (TEM, a model "JEM-2200-FS" JEOL Ltd.). The acceleration voltage was set to 200 kV. Nanoparticles were dropped on a TEM sample holder and air-dried to prepare a specimen.

Further, a dynamic light scattering method using an analytical device (a model "Nano-ZS" Malvernn Instruments Ltd.) was applied to analyze a hydrodynamic diameter of nanoparticles. Further, the charge of the surface of the nanoparticles was determined as a zeta potential.

Furthermore, a Ultraviolet-Visible spectrophotometer (model "UV-2100PC/3100PC," Shimadzu Corporation) was used to quantify the loading and release of a drug from nanoparticles.
(Animal Experiments)

Balb/c nu/nu mice were used for in vivo experiments. 48 mice were used for the experiments. These mice were conditioned for one week before the experiments, and then, G1-1 (RIKEN), which is a human glioblastoma cell line, was intracranially implanted (at 1 mm lower from bregma).

After the implantation, mice were randomly divided into 6 groups, each of which had 8 mice. After 96 hours of the implantation, each composition described below was intravenously administered to each mouse. Administration of each composition was conducted every 48 hours. The dose per administration was fixed at 16 μg of a drug.

The body weight of each mouse was measured every 5 days until it was sacrificed. After 48 hours of 10th administration of the composition, 4 mice of each group were euthanized and perfused, and the whole brain was isolated. The remaining 4 mice of each group were used for the measurement of survival rates. The isolated brains were fixed immediately with 4% paraformaldehyde. After 24 hours of the fixation, a brain specimen was transferred into a sucrose solution and allowed to stand overnight. Subsequently, the brain specimen was embedded in a resin (OCT compound) and frozen.

Next, a cryostat was used to prepare a brain specimen section with a thickness of 30 μm. The section was air-dried and hematoxylin-eosin stained. Further, the volume of a tumor was measured and recorded.

Example 1

Production Example 1

Nanoparticles were prepared by a modified method of lipid coacervation. 25 mg/mL (about $9.0 \times 10^{-3}$ mol/L) of 1,2-distearoyl-sn-glycero-3-phosphoethanolamine-N-[amino(polyethylene glycol)-2000] (DSPE-PEG(2000) amine, Avanti Polar Lipids, Inc.), 25 mg/mL (about $8.8 \times 10^{-2}$ mol/L) of stearic acid (Sigma-Aldrich Co., LLC.) and 25 g/mL (about $3.3 \times 10^{-2}$ mol/L) of lecithin (phosphatidylcholine) (Sigma-Aldrich Co., LLC.) were dissolved in chloroform and desiccated overnight to form a thin film.

Next, a solution of curcin in phosphate buffered saline (PBS) (pH 7.4, 5.33 mg/mL) was added to the thin film, and then sonication was performed gently (at 43 kHz) for a few minutes (1 to 2 minutes) with a sonicator (AS ONE Corporation) to prepare a transparent and stable suspension. Subsequently, the suspension was centrifuged at 50,000 rpm for 30 minutes to pelletize nanoparticles (washing process). This washing process was repeated, thereby obtaining nanoparticles of Production Example 1 (non-specific and non-targeted curcin-nanoparticles).

Production Example 2

(Preparation of RGD-Bound Curcin-Nanoparticles)

In the buffer solution, 1-ethyl-3-[3-dimentylaminopropyl] carbodiimide hydrochloride (EDC) (Sigma-Aldrich Co., LLC.) and N-hydroxysuccinimide (NHS) (Sigma-Aldrich Co., LLC.) were added to 2 mg of a tripeptide consisting of an amino acid sequence of arginine-glycine-aspartic acid (RGD tripeptide, Sigma-Aldrich Co., LLC.), and they were reacted and activated overnight at 4° C. by use of a tube rotator.

Next, the activated RGD tripeptide was reacted at 4° C. for 4 hours or longer (overnight) with added nanoparticles of Production Example 1 (10 mg). Subsequently, the suspension was centrifuged at 50,000 rpm to pelletize nanoparticles, thereby obtaining nanoparticles of Production Example 2 (RGD-bound curcin-nanoparticles).

Production Example 3

(Preparation of Transferrin-Bound Curcin-Nanoparticles)

In the buffer solution, EDC and NHS were added to 2 mg of transferrin (Sigma-Aldrich Co., LLC.), and they were reacted and activated overnight at 4° C. by use of a tube rotator.

Next, the activated transferrin was reacted at 4° C. for 4 hours or longer (overnight) with added nanoparticles of Production Example 1 (10 mg). Subsequently, the suspension was centrifuged at 50,000 rpm to pelletize nanoparticles, thereby obtaining nanoparticles of Production Example 3 (transferrin-bound curcin-nanoparticles).

Production Example 4

(Preparation of RGD and Transferrin-Bound Curcin-Nanoparticles)

The activated RGD tripeptide (corresponding to 1 mg of RGD tripeptide) prepared in the manner described in Production Example 2 and the activated transferrin (corresponding to 1 mg of transferrin) prepared in the manner described in Production Example 3 were reacted 4° C. for 4 hours or longer (overnight) with added nanoparticles of Production Example 1 (10 mg). Subsequently, the suspension was centrifuged at 50,000 rpm to pelletized nanoparticles, thereby obtaining nanoparticles of Production Example 4 (RGD and transferrin-bound curcin-nanoparticles).

Production Example 5

(Preparation of Drug-Void Nanoparticles)

Drug-void nanoparticles were prepared in the same manner as for Production Example 1 except that a PBS buffer was used instead of the solution of curcin in PBS.

Example 2

(Analysis of Nanoparticles)

The form of nanoparticles of Production Examples 1 to 4 was analyzed by a transmission electron microscope and a dynamic light scattering method.

The morphology of nanoparticles was observed by a transmission electron microscope (TEM, model "JEM-2200-FS" JEOL Ltd.). The acceleration voltage was set to 200 kV. Nanoparticles were dropped on a TEM sample holder and air-dried to prepare a specimen. FIG. 1 shows a typical transmission electron microscope image of nanoparticles of Production Examples 1 to 4. As shown in FIG. 1, nanoparticles of Production Examples 1 to 4 were nanoparticles having an egg-like globular shape. Nanoparticles of Production Example 1 (non-targeted curcin-nanoparticles) had a diameter of about 150 nm (average of 100 nanoparticles). It shows that nanoparticles each had an outer layer and vesicles enveloped by the outer layer.

Further, the hydrodynamic diameter of nanoparticles was analyzed by a dynamic light scattering method using an analytical device (model "Zetasizer Nano-ZS, Malvern Instruments Ltd.). The hydrodynamic diameter of nanoparticles as measured by a dynamic light scattering method is about 200 nm and a polydispersity index (PDI) is about 0.2. These results coincided with the transmission electron microscope image. The low PDI indicates that these nanoparticles are highly dispersed and not aggregated. The fact that particles are not aggregated indicates that these nanoparticles are very stable, which is an essential requirement for applying nanoparticles to therapeutic use.

Further, as the charge of the surface, zeta potential was measured by use of an analytical device (model "Zetasizer Nano-ZS, Malvern Instruments Ltd.). Nanoparticles of all of Production Examples 1 to 4 had a negative zeta potential. This indicates that these nanoparticles were hydrophilic. Nanoparticles of Production Examples 2 to 4 had a zeta potential that was slightly shifted to positive compared to nanoparticles of Production Example 1. It was considered that this resulted from the binding of RGD tripeptide or transferrin to surfaces of nanoparticles.

Table 1 shows hydrodynamic diameters and zeta potentials of nanoparticles of Production Examples 1 to 4 as determined by a dynamic light scattering method.

TABLE 1

| Nanoparticles | DLS (nm) | Zeta potential (mV) |
|---|---|---|
| Production Example 1 (non-targeted) | 147 ± 20 | −20 |
| Production Example 2 (RGD) | 160 ± 20 | −18 |
| Production Example 3 (Tf) | 183 ± 20 | −10 |
| Production Example 4 (RGD-Tf) | 192 ± 20 | −8 |

Example 3

(Study of Cell Compatibility)

Nanoparticles of Production Example 1 were contacted with culture cells and the survival rates of the cells were measured. As the cells, human umbilical vein endothelial cells (HUVEC), human cortical neuronal cell line (HCN-1A) and glioma cell line (G1-1) were used. HUVEC cells were obtained from Gibco. HCN-1A cells were obtained from ATCC (American Type Culture Collection). G1-1 cells (A172 cells) were obtained from RIKEN BioResource Research Center, Cell Engineering Division under Cell No. RCB2530.

Figure 2:
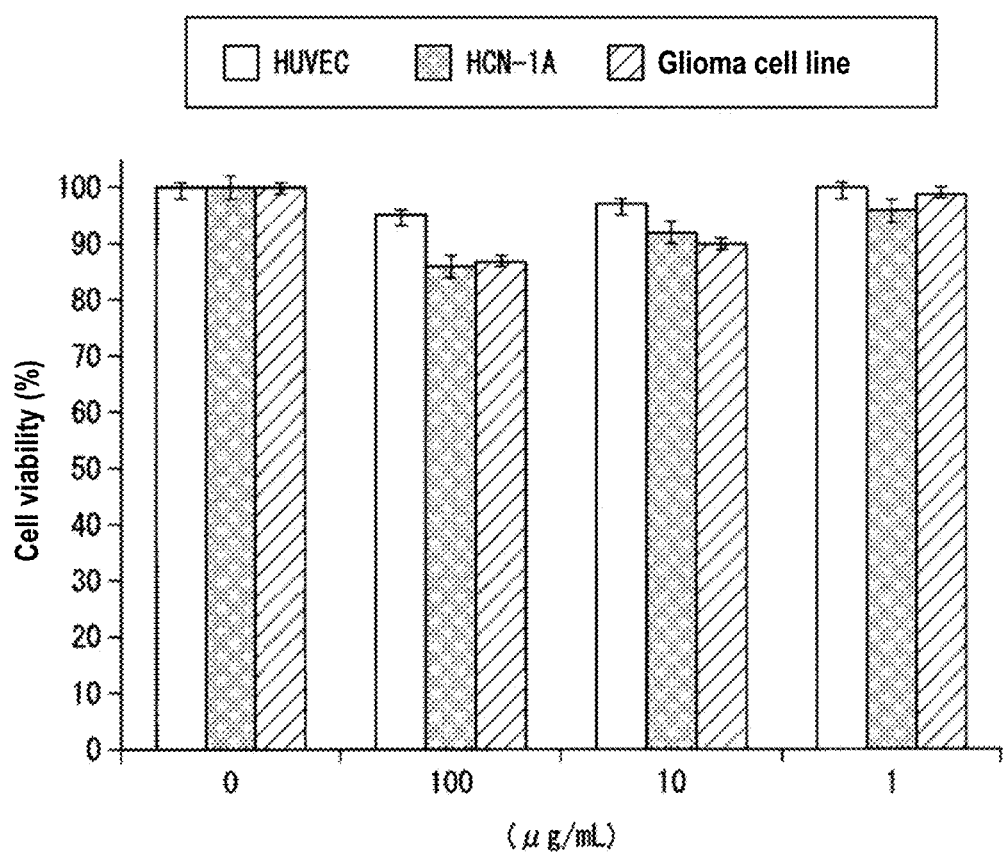
FIG. 2 is a graph showing measurements of cell viability in Example 3. The error bar represents the standard deviation (n=3).

To each medium of the cells, nanoparticles at a concentration of 0 (control), 1, 10 or 100 μg/mL were added, and then the cells were cultured for 72 hours. Thereafter, the survival rate of each cell line was measured by MTT assay. FIG. 2 shows graphs indicating the experimental results. The results have revealed that nanoparticles of Production Example 1 had low cytotoxicity and cell compatibility to various cells.

Example 4

(Loading and Release of Drug)

An Ultraviolet-Visible spectrometer (model "UV-2100PC/3100PC," Shimadzu Corporation) was used to quantify loading and release of a drug from nanoparticles. Loading of curcin (28 kDa) with nanoparticles of Production Examples 1 to 4 was confirmed by detection of characteristic peaks at 220 nm and 250 nm by ultraviolet-visible spectrum measurement and a band at 28 kDa observed by SDS polyacrylamide gel electrophoresis.

A slight peak shift was found in the ultraviolet-visible spectra of nanoparticles, and it was considered that this was caused by interaction between curcin and nanoparticle components. The loading efficiency of curcin to nanoparticles was about 67%. This has revealed that 3.5 mg of curcin (per 54.6 mg of nanoparticles) was loaded.

Release of curcin from nanoparticles was analyzed by ultraviolet-visible spectrum measurement. As a result, it has been revealed that the release of curcin long-continued. More specifically, the amount of release of curcin from nanoparticles was shown to be 32%, 51% and 83% at 24 hours later, 48 hours later and 72 hours later, respectively. It was considered that the release characteristic of curcin, which is highly gentle and sustained, was directly related to the morphology of nanoparticles.

Nanoparticles of Production Examples 1 to 4 load curcin with a bilayer membrane of a polymer and lipid. It was considered that curcin was not released unless curcin passed through this bilayer-membrane of lipid/polymer layers, and as a result, the sustained and delayed release of curcin was realized.

Example 5

(In Vivo Regression of Tumor)

Animal experiments were conducted in accordance with the above-described procedure. More specifically, free curcin alone, nanoparticles of Production Example 1 (curcin-nanoparticles), nanoparticles of Production Example 2 (RGD-bound curcin-nanoparticles), nanoparticles of Production Example 3 (transferrin-bound curcin-nanoparticles), or nanoparticles of Production Example 4 (RGD and transferrin-bound curcin-nanoparticles) were administered to Balb/c nu/nu mice (8 mice per group). Also, only a buffer was administered to a group as a control.

Specifically, 48 mice were used for the experiment. These mice were conditioned for one week before the experiment, and then, G1-1 (RIKEN), which is a human glioblastoma cell line, was intracranically implanted (at 1 mm below the bregma) in the mice. After the implantation, the mice were randomly divided into 6 groups, each of which had 8 mice. After 96 hours of the implantation, free curcin alone, nanoparticles of Production Example 1 (curcin-nanoparticles), nanoparticles of Production Example 2 (RGD-bound curcin-nanoparticles), nanoparticles of Production Example 3 (transferrin-bound curcin-nanoparticles), nanoparticles of Production Example 4 (RGD and transferrin-bound curcin-nanoparticles) were intravenously administered to Balb/c nu/nu mice (8 mice per group). Also, only a buffer was administered to a group as a control. Administration was repeatedly conducted every 48 hours. The dose per administration was fixed at 16 μg of the drug. The body weight of each mouse was measured every 5 days until it was sacrificed.

Figure 3:
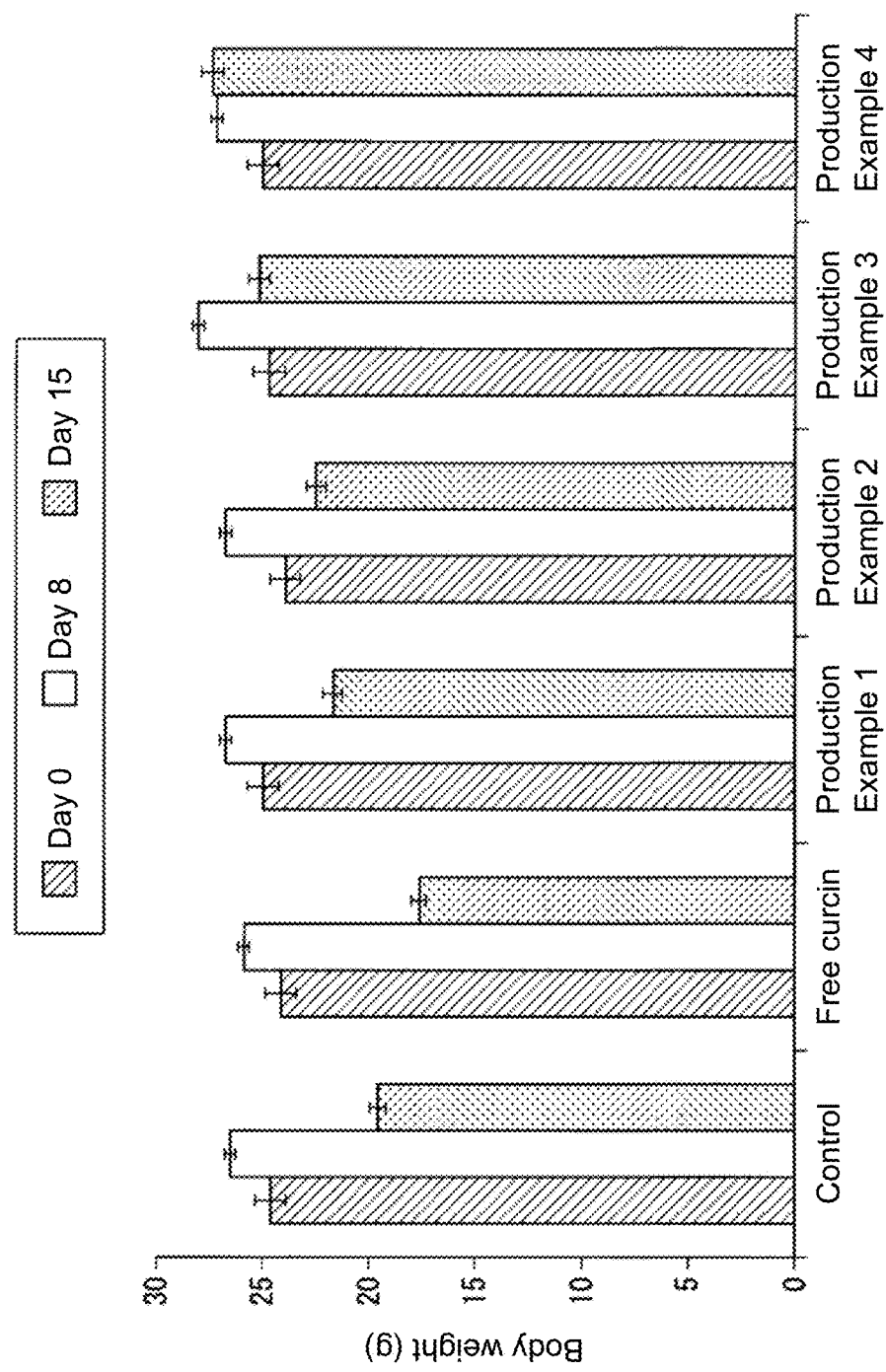
FIG. 3 is a graph showing changes in the weight of mice in Example 5. The error bar represents the standard deviation (n=3).

The body weight and the behavior of each mouse were recorded. FIG. 3 is a graph indicating changes of body weights of mice at day 0, day 8 and day 15 after the start of the experiment. As a result, it was shown that mice of the control group and the group having had administration of free curcin alone noticeably decreased their body weights at day 8 and day 15. The behaviors of the mice were also significantly changed. Main behaviors observed among the control group and the group having had administration free curcin alone include unbalanced actions, difficulty in taking diets or water, restricted movements, and delayed resistance or non-resistance against a contact.

Further, similar situations were observed among the group having had administration of nanoparticles of Production Example 1 (curcin-nanoparticles), but they were more improved compared to the control group and the group having had free curcin alone.

Further, among the groups having had administration of nanoparticles of Production Example 2 (RGD-bound curcin-nanoparticles) or nanoparticles of Production Example 3 (transferrin-bound curcin-nanoparticles), slight decreases of body weights were observed, but no abnormal behaviors were observed.

In addition, the group having had administration of nanoparticles of Production Example 4 (RGD and transferrin-bound curcin-nanoparticles) kept their body weights constant and displayed normal behaviors, thus exhibiting the healthiest condition.

Example 6

(Observation of Brain Specimen)

Figure 4:
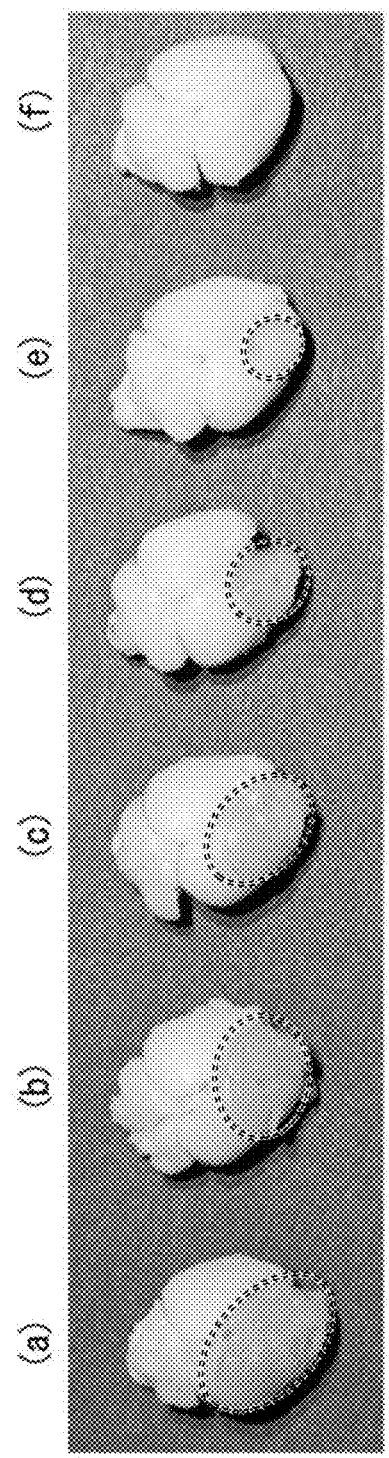
FIG. 4 is a photograph of a typical brain specimen of a mouse in each group in Example 6 ((a) to (f)).

After 48 hours of the 10th administration in Example 5, four mice of each group were euthanized; and the whole body of each mouse was perfused for fixation, and the whole brain was isolated. The growth of tumor in the isolated brain specimen was analyzed. In FIG. 4, (a) to (f) each shows a photograph of a typical brain specimen of mouse of each group. In FIG. 4(a) to (f), tumor zones are encircled by dotted lines. FIG. 4(a) is a photograph of a brain specimen of the control group; FIG. 4(b) is a photograph of a brain specimen of the group having had administration of free curcin alone; FIG. 4(c) is a photograph of a brain specimen of the group having had administration of nanoparticles of Production Example 1 (curcin-nanoparticles); FIG. 4(d) is a photograph of a brain specimen of the group having had administration of nanoparticles of Production Example 2 (RGD-bound curcin-nanoparticles); FIG. 4(e) is a photograph of a brain specimen of the group having had administration of nanoparticles of Production Example 3 (transferrin-bound curcin-nanoparticles); and FIG. 4(f) is a photograph of a brain specimen of the group having had administration of nanoparticles of Production Example 4 (RGD and transferrin-bound curcin-nanoparticles).

As a result, brain specimens of the control group and the group having had administration of only free curcin showed tumorigenic transformation of almost the entire of one lobe. Further, tumor was metastasized to the other lobe, indicating high invasiveness of glioma.

The group having had administration of nanoparticles of Production Example 1 showed tumorigenic transformation of about ¼ of brain. Further, in the groups having had administration of nanoparticles of Production Examples 2 and 3, the tumor volume of the group having had administration of nanoparticles of Production Example 3 was relatively small, while the tumor volume of the group having had administration of nanoparticles of Production Example 2 was relatively large. Further, the group having had administration of nanoparticles of Production Example 4 was the most successful group in the treatment and no tumor that was confirmed by the naked eye was found on the surface of the brain. The results show that nanoparticles of Production Example 4 were very effective in suppressing the growth of brain tumor.

Example 7

(Histopathologic Analysis of Brain Specimen)

The brain isolated in Example 6 was immediately fixed with 4% paraformaldehyde. After 24 hours of the fixation, a brain specimen was transferred into a sucrose solution and allowed to stand overnight. Subsequently, the brain specimen was embedded in a resin (OCT compound) and frozen. Next, a cryostat was used to prepare a brain specimen section with a thickness of 30 μm. The section was air-dried and hematoxylin-eosin stained. Further, the volume of a tumor was measured and recorded.

Figure 5:
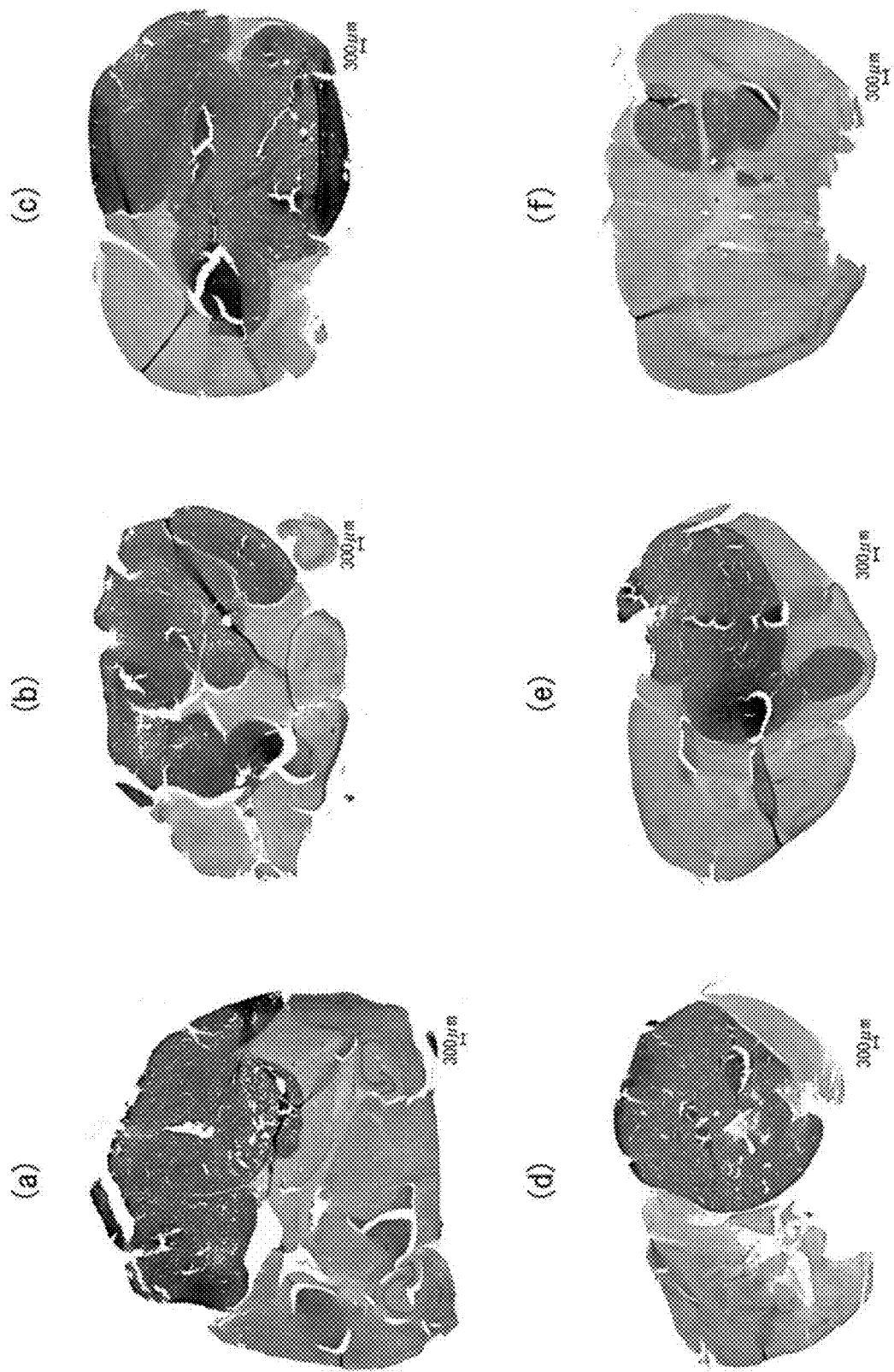
FIG. 5 is a photograph of a hematoxylin-eosin stain result of a section of the central portion of tumor in a brain specimen of each group in Example 7 ((a) to (f)).

FIG. 5(a) to (f) are photographs showing a hematoxylin-eosin stain result of a section of the central portion of tumor in a brain specimen of each group. FIG. 5(a) is a photograph of the brain specimen of the control group; FIG. 5(b) is a photograph of the brain specimen of the group having had administration of free curcin alone; FIG. 5(c) is a photograph of the brain specimen of the group having had administration of nanoparticles of Production Example 1 (curcin-nanoparticles); FIG. 5(d) is a photograph of the brain specimen of the group having had administration of nanoparticles of Production Example 2 (RGD-bound curcin-nanoparticles); FIG. 5(e) is a photograph of the brain specimen of the group having had administration of nanoparticles of Production Example 3 (transferrin-bound curcin-nanoparticles); and FIG. 5(f) is a photograph of the brain specimen of the group having had administration of nanoparticles of Production Example 4 (RGD and transferrin-bound curcin-nanoparticles).

As a result, the brain specimen of the mouse of the control group showed tumor invasion into about a half of the brain. Further, the brain was enlarged to about twice the normal brain, and the morphological structure was changed.

Further, among the brains except that of the group having had administration of nanoparticles of Production Example 4, the invasion of tumor, which may be a serious threat on the survival and the prognosis, was found. The brain of the group having had administration of nanoparticles of Production Example 4 had a smaller volume of tumor compared to the control group and the group having had administration of free curcin alone.

Figure 6:
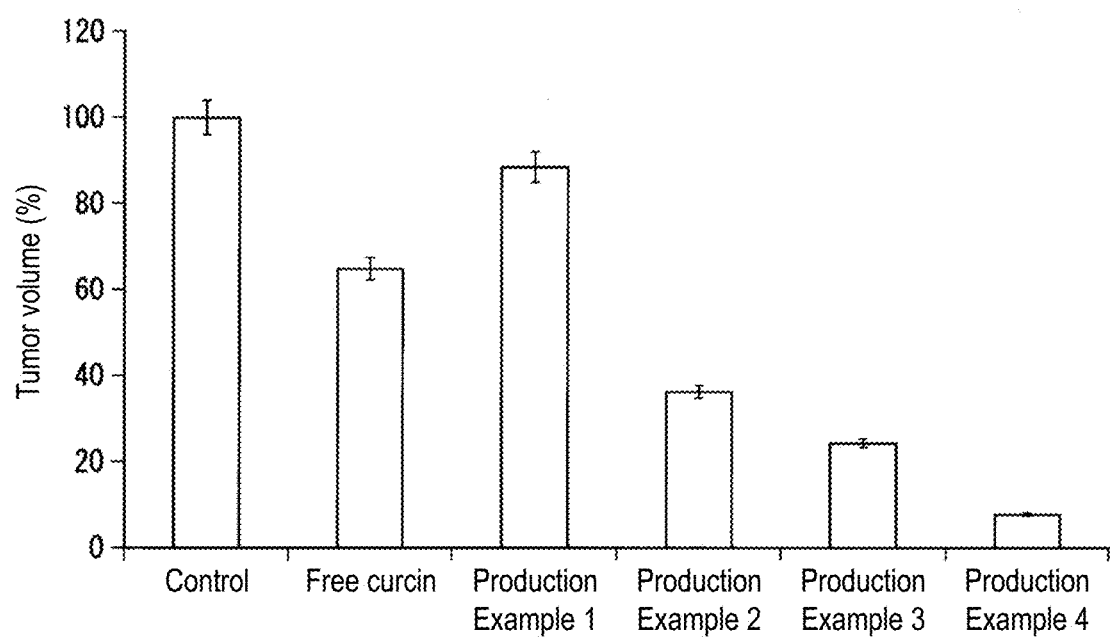
FIG. 6 is a graph showing measurements of the tumor volume in the brain specimen of each group in Example 7. The error bar represents the standard deviation (n=3).

FIG. 6 is a graph indicating results of measured volumes of tumor in the brain specimens of each group. As a result of statistical analysis, the tumor volume of the group having had administration of free curcin alone was about 70% of the tumor volume of the control group. No regression of tumor was found even in the group having had administration of nanoparticles of Production Example 1. Further, the tumor volume of the group having had administration of nanoparticles of Production Example 2 was about 40% of the tumor volume of the control group. The tumor volume of the group having had administration of nanoparticles of Production Example 3 was about 25% of the tumor volume of the control group.

In contrast, the tumor volume of the group having had administration of nanoparticles of Production Example 4 was about 10% of the tumor volume of the control group, and there was found a statistically significant difference between them.

The above results indicate that nanoparticles of Production Examples 1 to 4 were able to pass through the blood brain barrier and reach brain tumor depending on the efficiency of ligands placed on the surface of nanoparticles (ability to selectively and specifically bind to target cells). In particular, the above results have indicated that nanoparticles of Production Example 4 (RGD and transferrin-bound curcin-nanoparticles) had an excellent therapeutic effect on brain tumor.

Example 8

(Study on Extension of Survival Period)

The remaining 4 mice of each group, which were not euthanized in Example 6, were used to determine survival rates. The survival period of mice of each group was determined. Table 2 shows determined survival periods. As a result, the survival periods of mice of the control group and the group having had administration of free curcin alone were about 20 days from the implantation of cancer.

Further, the survival period of mice of the group having had administration of nanoparticles of Production Example 2 was extended by about 5 days compared to the control group. Further, the survival period of mice of the group having had administration of nanoparticles of Production Example 3 was extended by about 10 days compared to the control group. In contrast, the survival period of mice of the group having had administration of nanoparticles of Production Example 4 was extended about twice compared to the control group.

The analytical results of the brain specimens show that tumor in the group having had administration of nanoparticles of Production Example 4, was remarkably reduced in the volume but not disappeared. It was considered that the death of mice after 40 days of the implantation of tumor was due to the remaining of tumor cells and the recurrence of tumor. It was considered that extension of the treatment period could possibly eliminate the remaining tumor cells completely.

TABLE 2

| Group | Survival period |
| --- | --- |
| Control group | All mice died till day 20. |
| Group having had administration of free curcin alone | All mice died till day 20. |
| Group having had administration of nanoparticles of Production Example 1 | 25% of mice died till day 15 and 75% of mice died till day 20. |
| Group having had administration of nanoparticles of Production Example 2 (RGD) | 25% of mice died till day 20 and 75% of mice died till day 25. |
| Group having had administration of nanoparticles of Production Example 3 (transferrin) | 25% of mice died till day 20 and 75% of mice died till day 30. |
| Group having had administration of nanoparticles of Production Example 4 (RGD and transferrin) | All mice died till day 40. |

Example 9

(Further Analysis of Nanoparticles)

Figure 7:
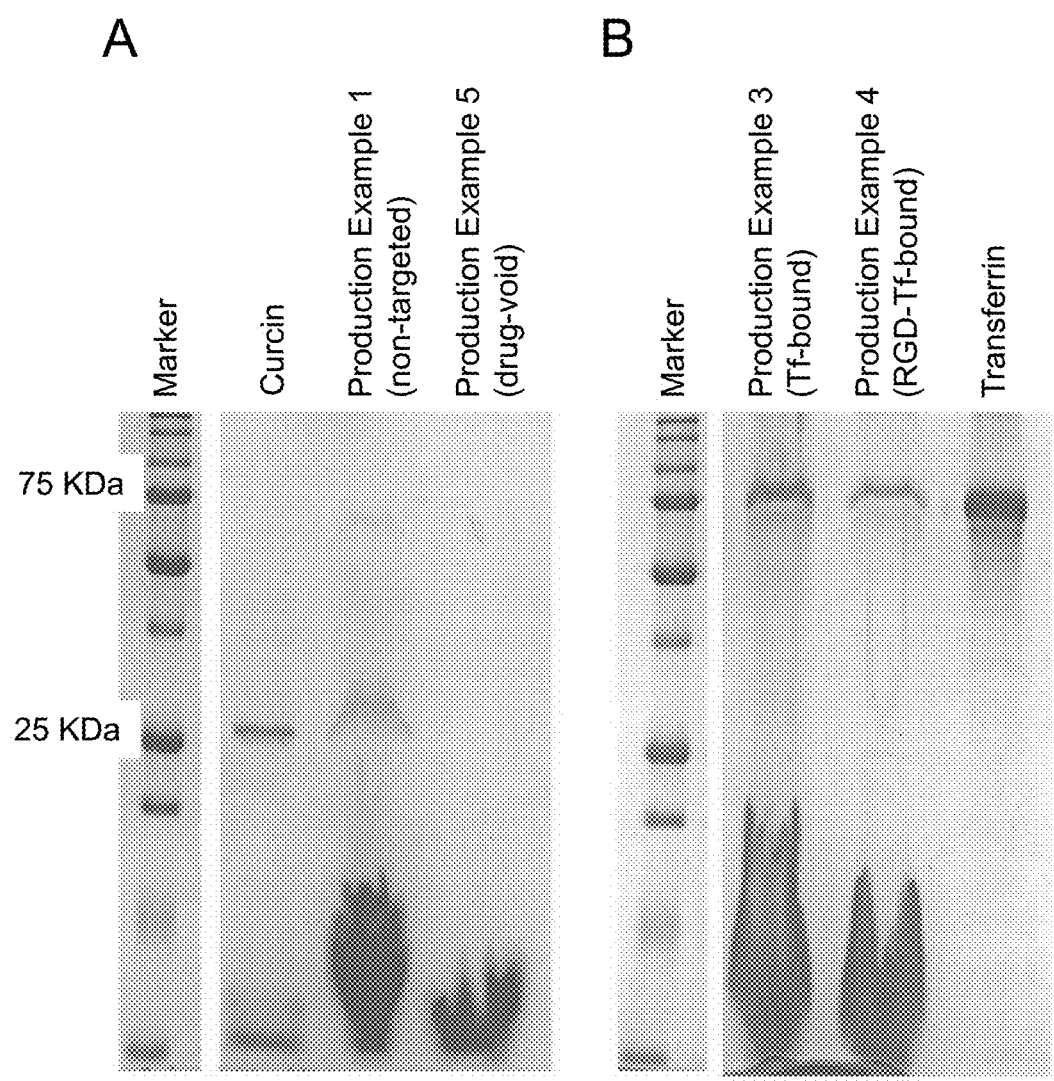
FIG. 7 is a photograph of SDS-PAGE gel showing the uptake (binding) of curcin or transferrin to nanoparticles shown in Example 9 ((A) and (B)).

Uptake of curcin with nanoparticles was confirmed using SDS-PAGE. Curcin, nanoparticles of Production Example 5 (drug-void nanoparticles), and nanoparticles of Production Example 1 (non-targeted curcin-nanoparticles) were subjected to SDS-PAGE, and the gel was stained for protein analysis. Results are shown in FIG. 7A. Curcin has a molecular weight of 28 kDa. The band at 28 kDa was observed for nanoparticles of Production Example 1, and this indicated the uptake of curcin with nanoparticles of Production Example 1. In contrast, no band at 28 kDa was observed for nanoparticles of Production Example 5 (drug-void nanoparticles).

Binding of transferrin to nanoparticles was confirmed using SDS-PAGE. Transferrin, nanoparticles of Production Example 3 (transferring-bound curcin-nanoparticles) and nanoparticles of Production Example 4 (RGD and transferrin-bound curcin-nanoparticles) were subjected to SDS-PAGE, and the gel was stained for protein analysis. Results are shown in FIG. 7B. The band of transferrin at 79 kDa was found in all lanes, indicating that transferrin was bound to nanoparticles of Production Examples 3 and 4.

Figure 8:
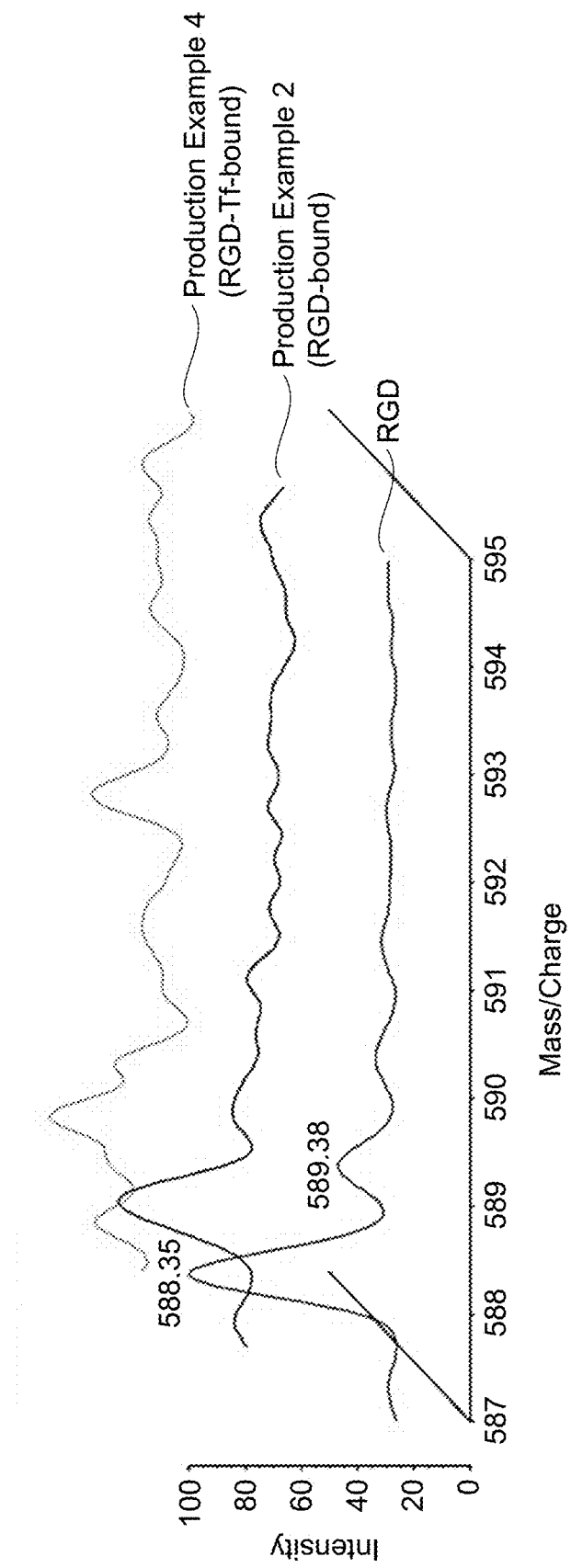
FIG. 8 is a graph showing measurements with MALDI, which indicate the binding of RGD tripeptide to nanoparticles in Example 9.

Next, binding of RGD tripeptide on the surface of nanoparticles was confirmed by MALDI (matrix-assisted laser desorption ionization) mass spectrometry. RGD tripeptide, particles of Production Example 2 (RGD-bound curcin-nanoparticles) and particles of Production Example 4 (RGD and transferrin-bound curcin-nanoparticles) were analyzed by a MALDI mass spectrometer (AXIMA®-CFR, Kratos Analytical, Shimadzu Corporation). Results are shown in FIG. 8. Although being slightly shifted from 568 m/z, at which RGD tripeptide usually exhibits a peak, RGD tripeptide exhibited a peak at 588.35 m/z. Nanoparticles of Production Example 2 (RGD-bound curcin-nanoparticles) and nanoparticles of Production Example 4 (RGD and transferrin-bound curcin-nanoparticles) exhibited a peak at the same position as RGD tripeptide. This indicates that RGD tripeptide was present in nanoparticles of Production Example 2 (RGD-bound curcin-nanoparticles) and nanoparticles of Production Example 4 (RGD and transferrin-bound curcin-nanoparticles).

Example 10

(Further Study on Extension of Survival Period)

4 week-old Balb/c nu/nu mice were conditioned for 2 weeks, and then human glioblastoma cell line G1-1 (RIKEN) were intracranially implanted at 30,000 cells per mouse to produce intracranial tumor-bearing mice. After the implantation, the mice were injected into tail vein with any of PBC (negative control), free curcin (16 μg per mouse), and nanoparticles of Production Examples 1 to 4 (250 μg of nanoparticles containing about 16 μg of curcin in 100 μl). The administration was conducted once every 2 days for a total of 18 administrations.

Figure 9:
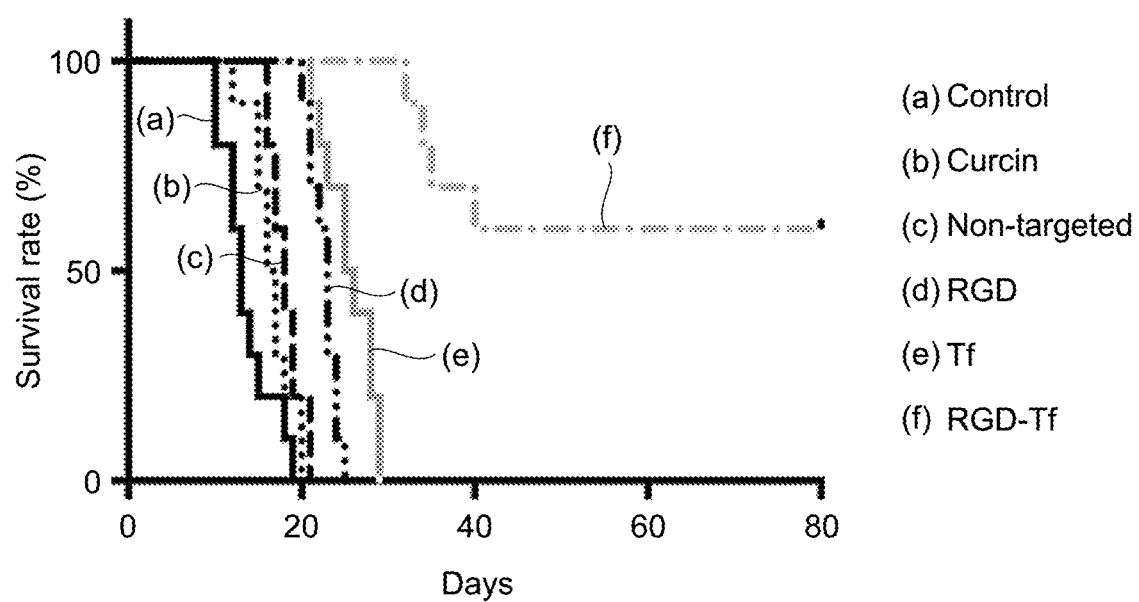
FIG. 9 is a graph showing the survival rates of mice of each group in Example 10.

The survival periods of the mice are seen in FIG. 9. The survival rates are shown in FIG. 9(a) for the control group; FIG. 9(b) for the free curcin-administered group; FIG. 9(c) for the group having had administration of nanoparticles of Production Example 1 (non-targeted curcin-nanoparticles); FIG. 9(d) for the group having had administration of nanoparticles of Production Example 2 (RGD-bound curcin-nanoparticles); FIG. 9(e) for the group having had administration of nanoparticles of Production Example 3 (transferrin-bound curcin-nanoparticles); and FIG. 9(f) for the group having had administration of nanoparticles of Production Example 4 (RGD and transferrin-bound curcin-nanoparticles). The vertical axis of FIG. 9 indicates the survival rate (%) and the horizontal axis of FIG. 9 indicates days after the implantation taking the day for implantation as day 0.

About 60% of the mice having had administration of nanoparticles of Production Example 4 (RGD and transferrin-bound curcin-nanoparticles) exhibited complete tumor regression and survived until day 80 without health-related abnormalities (FIG. 9(f)) (mice were euthanized after day 80). In contrast, the mice from all the other groups did not keep alive for 30 days or more. The results show that RGD and transferrin-bound curcin-nanoparticles have an excellent therapeutic effect on brain tumor and greatly extended the survival period.

Example 11

Production Example 6

(Preparation of Non-Targeted QD-Nanoparticles)

CdSe QDs (quantum dot) were prepared according to the method described in Mohamed, et al., Nanoscale, 2016, 8, 7876 to 7888. Specifically, 0.0078 g of selenium (Se) was dissolved at 250° C. for 30 minutes in 1 mL of an oil extracted from seeds of *Jatropha curcas* (JC oil) to prepare a selenium precursor solution; and this solution was cooled to room temperature. A mixture of cadmium oxide (CdO) powder (0.1 mmol), JC oil (5 mL) and octadecene (10 mL) was stirred and heated to 300° C. under the flow of argon until a solution thereof became transparent. Next, the selenium precursor solution was quickly added to the mixture and kept at 300° C. for 2 minutes, and was immediately cooled down to room temperature. Further, the mixture was centrifuged at 9,000 rpm for 5 minutes with ethanol and washed twice; and the obtained quantum nanocrystals were suspended in chloroform.

The QDs (quantum dots) suspended in chloroform were added to DSPE-PEG(2000) Amine, stearic acid and lecithin dissolved in chloroform at equal concentrations, and desiccated overnight to form a thin film. Next, a PBS buffer (pH 7.4) was added to the thin film, and then sonication (hydration) was performed gently (at 43 kHz) for a few minutes (1 to 2 minutes) with a sonicator (AS ONE Corporation) to prepare a transparent and stable suspension. Subsequently, the suspension was centrifuged at 50,000 rpm for 30 minutes to pelletize nanoparticles, thereby obtaining nanoparticles of Production Example 6 (non-targeted QD-nanoparticles).

Production Example 7

(Preparation of RGD-Bound QD-Nanoparticles)

Nanoparticles of Production Example 7 (RGD-bound QD-nanoparticles) were prepared by the same method as in Production Example 2 except that nanoparticles of Production Example 6 were used instead of nanoparticles of Production Example 1.

Production Example 8

(Preparation of Transferrin-Bound QD-Nanoparticles)

Nanoparticles of Production Example 8 (transferrin-bound QD-nanoparticles) were prepared by the same method as in Production Example 3 except that nanoparticles of Production Example 6 were used instead of nanoparticles of Production Example 1.

Production Example 9

(Preparation of RGD and Transferrin-Bound QD-Nanoparticles)

Nanoparticles of Production Example 9 (RGD and transferrin-bound QD-nanoparticles) were prepared by the same method as in Production Example 4 except that nanoparticles of Production Example 6 were used instead of nanoparticles of Production Example 1.

Example 12

(Accumulation of Nanoparticles in Tumor)

This experiment used intracranial tumor-bearing mice prepared as described in Example 10. The mice were intravenously injected with any of PBS (negative control), fluorescent curcin (100 μg per mouse), and nanoparticles of Production Examples 6 to 9 (0.5 mg of nanoparticles per mouse). The fluorescent curcin was prepared using a commercially available NHS ester of ICG (indocyanine green dye). Purified curcin and NHS-ICG (Dojindo) were reacted with each other at 37° C. for 30 minutes for conjugation, and the fluorescent curcin was obtained by separation from free curcin and dye by molecular-weight cut-off based centrifugation according to recommendations by the manufacturer. After 6, 24 and 48 hours of the administration, the mice were euthanized and the brains were isolated. QD accumulation in tumor and normal brain tissue was imaged using an in vivo imaging system (model of "Clairvivo Opt", Shimadzu Corporation). After imaging, the tumor was separated from the normal brain tissue; each of the tumor and the normal brain tissue was homogenized; and fluorescence of QDs was measured using a fluorescence spectrophotometer.

Figure 10:
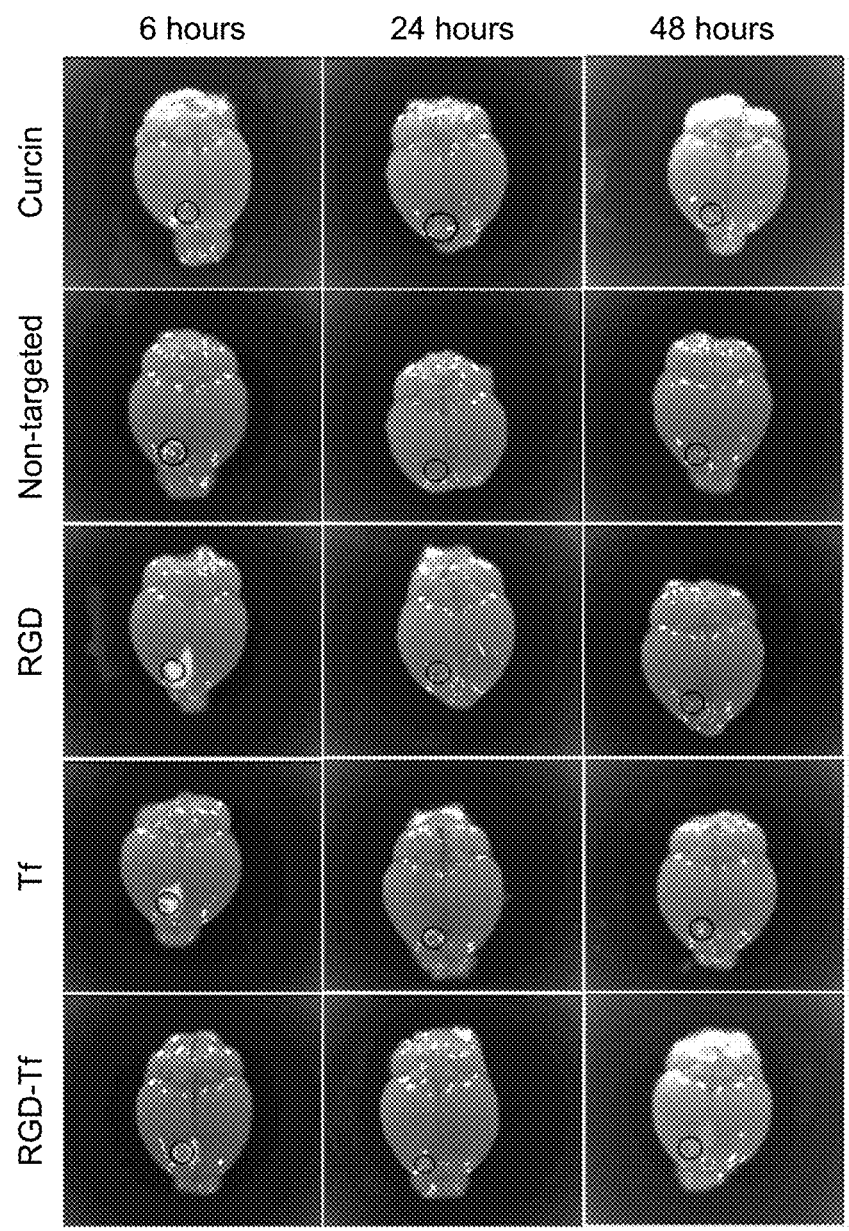
FIG. 10 is a photograph showing accumulations of QD (quantum dot) nanoparticles in the brain of each group in Example 12.

FIG. 10 shows accumulations of QD-nanoparticles in the brains. The control group did not exhibit, as expected, fluorescence in the tumor and the normal brain. The brain of the curcin-administered group showed non-specific accumulation of curcin in both the tumor and the normal brain tissue, but the fluorescence intensity in the tumor was very low. Nanoparticles of Production Example 9 (RGD and transferrin-bound QD-nanoparticles) exhibited red-imaged and distinct fluorescent signal after 6 hours of the administration within the tumor tissue while non-specific accumulation was not found in adjacent normal brain tissue. Nanoparticles of Production Examples 7 and 8 (RGD-bound QD-nanoparticles and transferrin-bound QD-nanoparticles) also exhibited tumor specific accumulation by 6 hours. After 24 hours, the QD signal intensity was diminished in many groups, but the intensity of nanoparticles of Production Example 9 (RGD and transferrin-bound QD-nanoparticles) was kept high. By 48 hours, most of the QDs were cleared from the tumor, while only nanoparticles of Production Example 9 (RGD and transferrin-bound QD-nanoparticles) exhibited detectable fluorescence.

Figure 11:
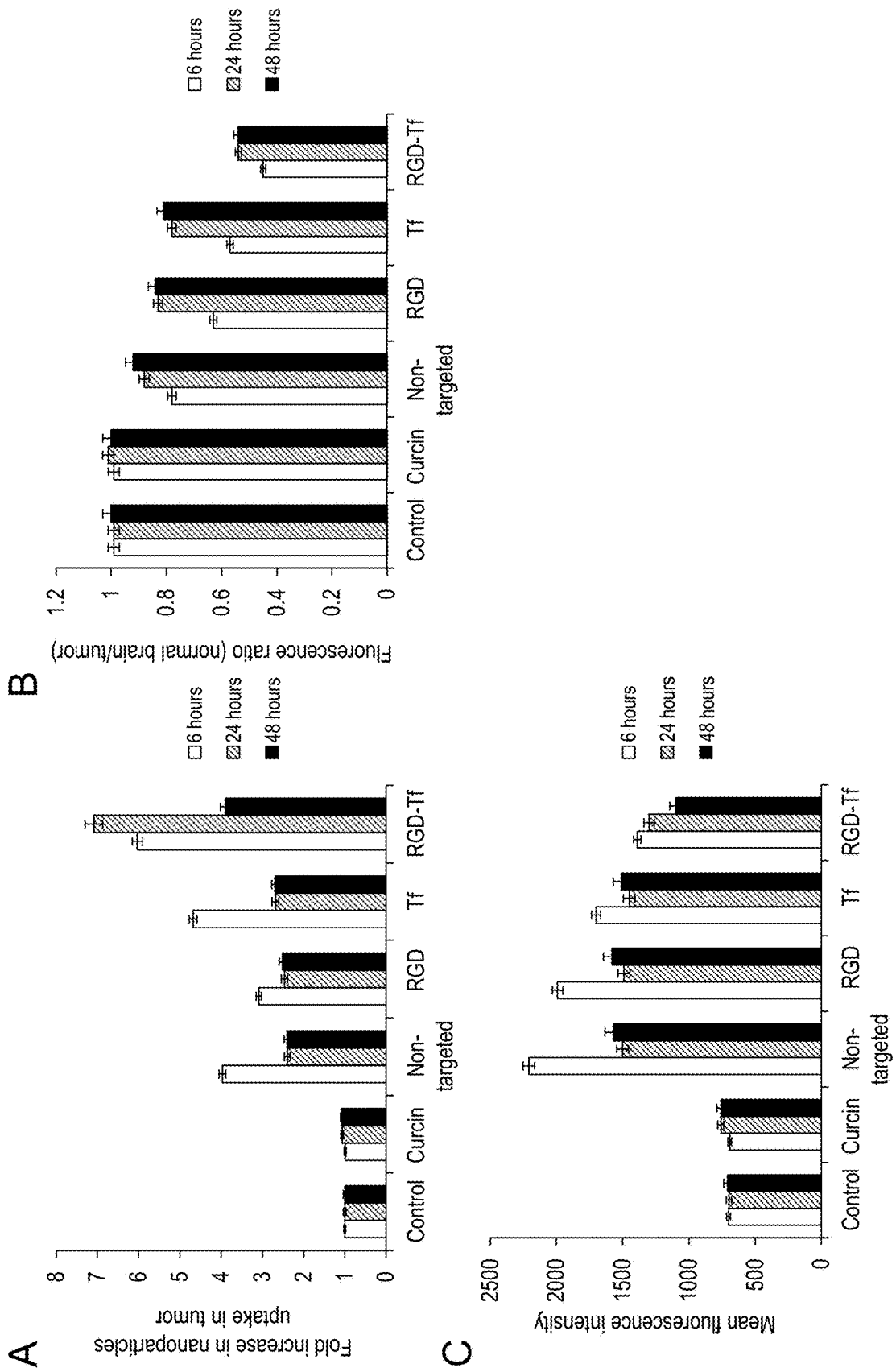
FIG. 11 is a graph showing accumulations of nanoparticles in the tumor in each group in Example 12 ((A) to (C)). The error bar represents the standard deviation (n=3).

The fluorescence in the tumor of each group was quantified, and results are shown in FIG. 11A in comparison with the control group. Nanoparticles of Production Example 6 (non-targeted QD-nanoparticles), nanoparticles of Production Example 7 (RGD-bound QD-nanoparticles), nanoparticles of Production Example 8 (transferrin-bound QD-nanoparticles) and nanoparticles of Production Example 9 (RGD and transferrin-bound QD-nanoparticles) exhibited an increase of nanoparticle accumulation by 4, 3.5, 4.8 and 5.8 fold compared with the control, respectively, after 6 hours of the administration. After 24 hours of the administration, nanoparticles of Production Example 6 (non-targeted QD-nanoparticles), nanoparticles of Production Example 7 (RGD-bound QD-nanoparticles) and nanoparticles of Production Example 8 (transferrin-bound QD-nanoparticles) exhibited decreased fluorescence intensity compared with those after 6 hours. In contrast, the intensity for the nanoparticles of Production Example 9 (RGD and transferrin-bound QD-nanoparticles) further increased after 24 hours, which was about 7 times higher than the control. This result shows that RGD and transferrin-bound nanoparticles were delivered to brain tumor and accumulated in the tumor for a long period.

FIG. 11B shows fluorescence ratio between normal brain tissue and tumor tissue. When nanoparticles accumulate non-specifically, the normal brain tissue and the tumor exhibit a similar accumulation profile, and in consequence, the fluorescence ratio between them becomes nearly 1. Conversely, when nanoparticles accumulate specifically in the tumor, the ratio becomes lower. After 6 hours of the administration, nanoparticles of Production Example 6 (non-targeted QD-nanoparticles) had a ratio of about 0.8; while nanoparticles of Production Example 7 (RGD-bound QD-nanoparticles), nanoparticles of Production Example 8 (transferrin-bound QD-nanoparticles) and nanoparticles of Production Example 9 (RGD and transferrin-bound QD-nanoparticles) had ratios of 0.67, 0.57 and 0.5, respectively. This shows that RGD and transferrin-bound nanoparticles accumulated in a tumor-specific manner and non-specific accumulation in the normal brain tissue was very small. After 24 hours and 48 hours of the administration, the ratio was increased in many groups, but the ratio for nanoparticles of Production Example 9 (RGD and transferrin-bound QD-nanoparticles) remained about 0.6 even after 48 hours. This shows that RGD and transferrin-bound nanoparticles accumulate specifically in the tumor over a long period.

FIG. 11C shows the mean fluorescence intensity in the normal brain tissue. This result shows non-specific accumulation of fluorescent curcin or particles in the brain tissue. The control group exhibited almost no fluorescence in the brain tissue. The fluorescent curcin group also exhibited almost no fluorescence in the brain. This shows that the passage of free drug through the blood-brain barrier is restricted. Nanoparticles of Production Example 6 (non-targeted QD-nanoparticles) exhibited the highest non-specific accumulation in the brain, followed by nanoparticles of Production Example 7 (RGD-bound QD-nanoparticles) and then nanoparticles of Production Example 8 (transferrin-bound QD-nanoparticles). Nanoparticles of Production Example 9 (RGD and transferrin-bound QD-nanoparticles) had a very small non-specific accumulation in the normal brain tissue.

The above results show that RGD and transferrin-bound nanoparticles accumulate in the brain tumor over a long period and has a small non-specific accumulation in the normal brain tissue.

Example 13

(Biodistribution of Nanoparticles)

The experiment used intracranial tumor-bearing mice prepared as described in Example 10. The mice were injected into tail vein with any of nanoparticles of Production Examples 6 to 9 (0.5 mg of nanoparticles per mouse). After 6, 24 and 48 hours of the injection, the mice were euthanized; major organs (brain, lungs, heart, kidney, spleen and liver) were isolated; and further, tumor in the brain was separated from the normal brain tissue. Further, blood was collected from the mice. The QD accumulation was quantified by use of ICP-MS (inductively coupled plasma mass spectrometry) (Thermo Scientific K.K.) based on the elemental composition of quantum dots.

Figure 12:
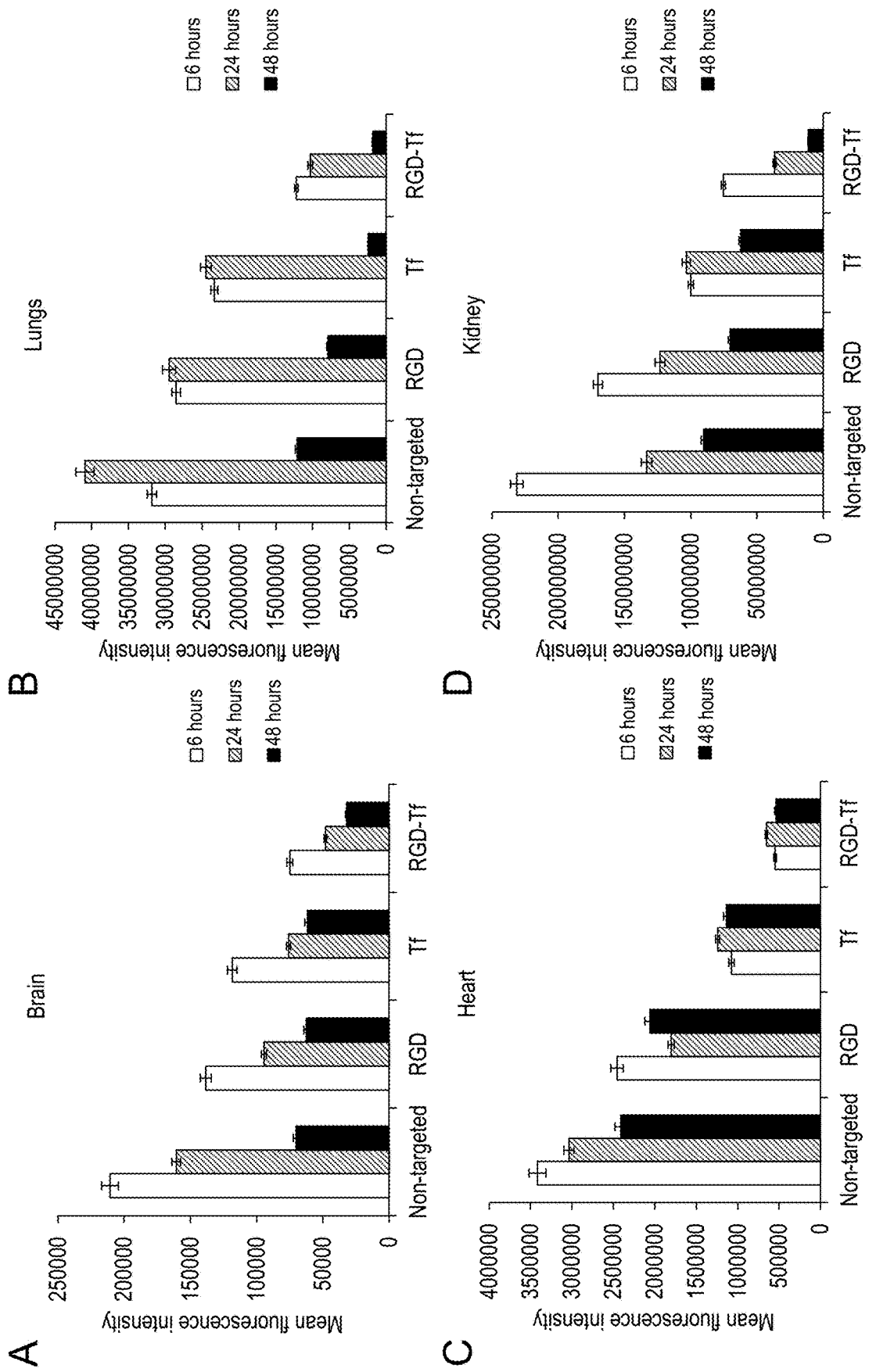
FIG. 12 is a graph showing the mean fluorescence intensity in each organ in each group in Example 13. The error bar represents the standard deviation (n=3).
Figure 13:
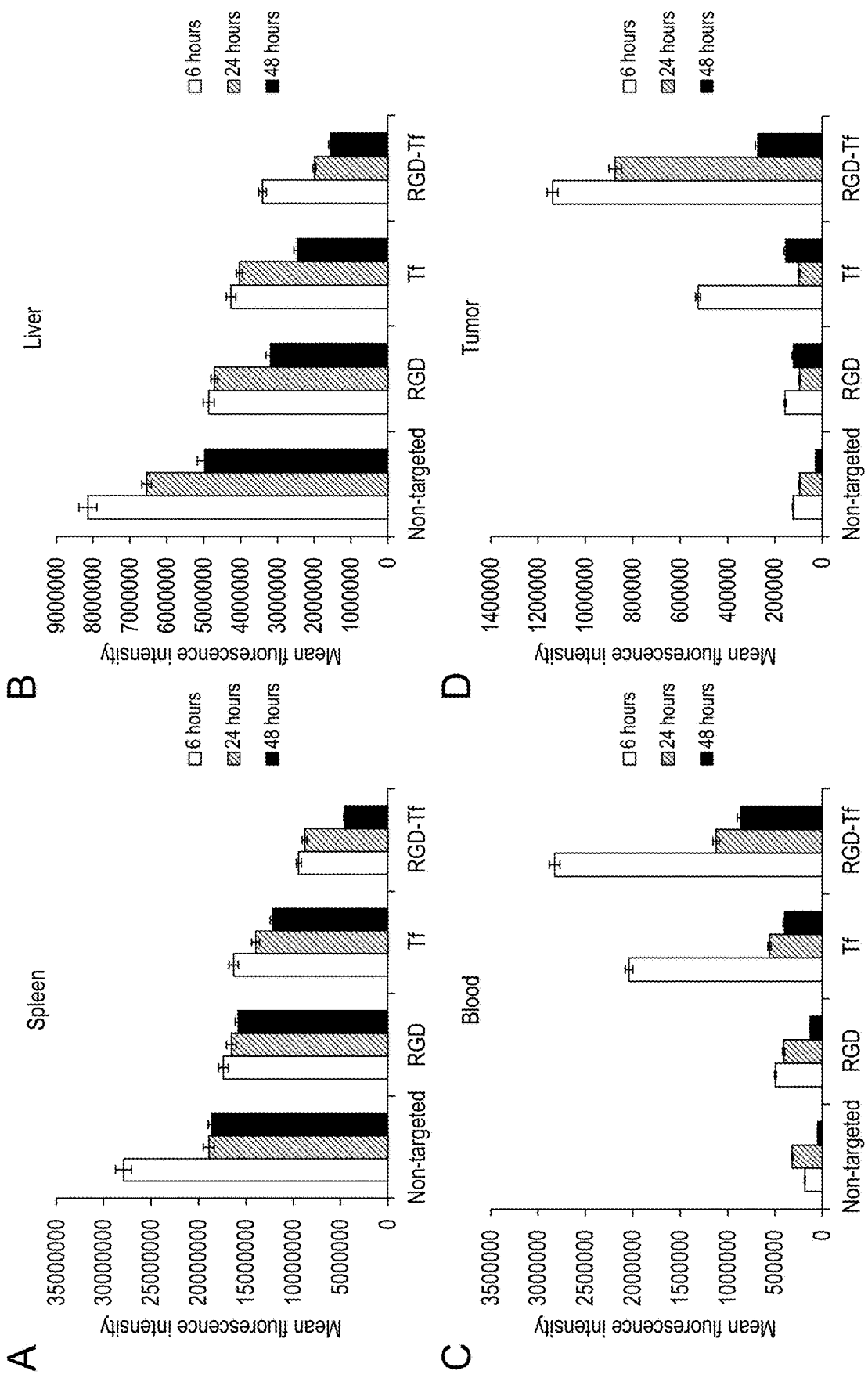
FIG. 13 shows graphs showing the mean fluorescence intensity in each organ, blood and tumor in each group in Example 13 ((A) to (D)). The error bar represents the standard deviation (n=3).

Results are shown in FIGS. 12 and 13. The mean fluorescence intensity of each group is shown in FIG. 12A for the brain; FIG. 12B for the lungs; FIG. 12C for the heart; FIG. 12D for the kidney; FIG. 13A for the spleen; FIG. 13B for the liver; FIG. 13C for the blood; and FIG. 13D for the tumor.

Nanoparticles of Production Example 9 (RGD and transferrin-bound QD-nanoparticles) had lower accumulations in the normal brain tissue, lungs, heart, kidney, spleen and liver than nanoparticles of Production Examples 6 to 8; and this shows a lower non-specific accumulation (FIGS. 12A to 12D and 13A to 13B). Nanoparticles of Production Example 6 (non-targeted QD-nanoparticles) had the highest non-specific accumulation, followed by nanoparticles of Production Example 7 (RGD-bound QD-nanoparticles) and then nanoparticles of Production Example 8 (transferrin-bound QD-nanoparticles). On the other hand, a very large amount of nanoparticles of Production Example 9 (RGD and transferrin-bound QD-nanoparticles) was detected in the blood and the tumor (FIGS. 13C and 13D). The presence of a large amount of nanoparticles of Production Example 9 in the blood indicates that these particles have an increased blood half-life compared to other particles. Further, nanoparticles of Production Example 9 (RGD and transferrin-bound QD-nanoparticles) were present in the tumor in an amount of about 6 to 7 times as much as nanoparticles of Production Example 6 (non-targeted QD-nanoparticles); of 6 times as much as nanoparticles of Production Example 7 (RGD-bound QD-nanoparticles) and of about two times as much as nanoparticles of Production Example 8 (transferrin-bound QD-nanoparticles). This result shows that RGD and transferrin-bound nanoparticles have high targeting efficiency and specificity to the tumor.

Example 14

(Production of In Vitro BBB Model)

Figure 14:
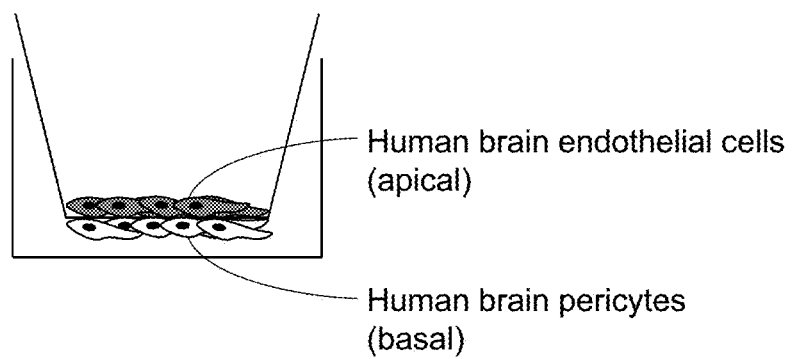
FIG. 14 is a schematic view of an in vitro BBB model of Example 14.

Human brain microvascular endothelial cells and human microvascular pericytes were purchased from Cell Systems and cultured using CSC classic medium kit. The cells were grown at 37° C. in humidified atmosphere and 5% $CO_2$. A Transwell® insert (pore size of 3 µm, 24 wells, BD Falcon) was placed in an inverted manner and the pericytes were added thereon and grown for 24 hours. Thereafter, the insert was inverted again (put back) with care and placed in a 24-well plate, and the endothelial cells were seeded on the upper side of the insert. The cells were cultured until a high density of coculture was achieved, and an in vitro BBB (blood brain barrier) model was produced (FIG. 14). This in vitro BBB model had human brain endothelial cells cultured at the upper side (apical side) of a membrane and human brain pericytes cultured at the lower side (basal side). In subsequent experiments using the in vitro BBB model, Transwell® inserts with no cells were utilized as a negative control.

Example 15

(Evaluation of In Vitro BBB Model)

In order to confirm the BBB integrity of the in vitro BBB model produced in Example 14, medium permeation assay and apical-to-basal permeability analysis were carried out.

The medium permeation assay was conducted by adding 0.5 ml of media to an upper chamber of the in vitro BBB model, and 30 minutes later, quantifying a volume of the medium that permeated to a lower chamber. As a negative control, a Transwell® insert with no cells was utilized. A lower permeation volume of medium indicates the presence of tighter BBB junctions.

Figure 15:
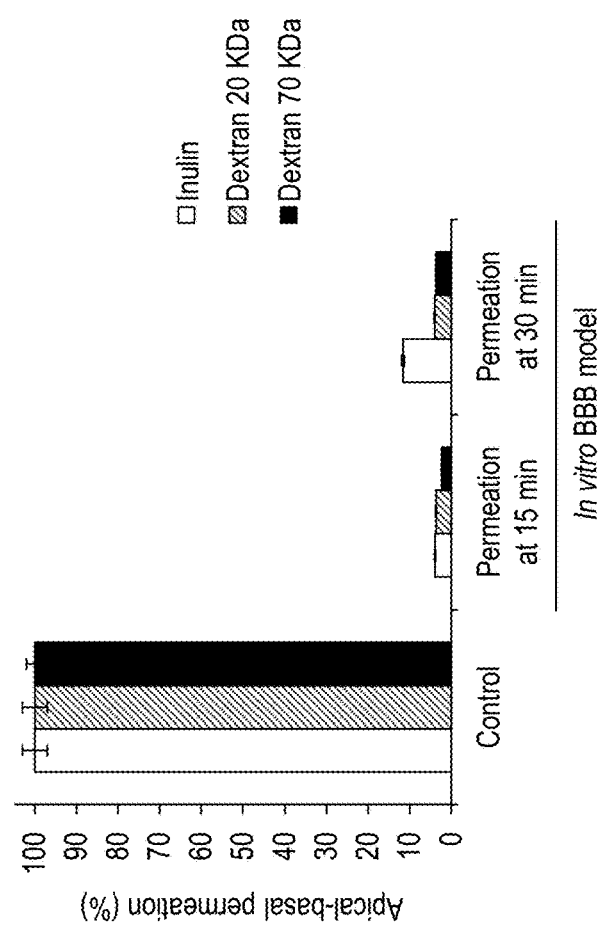
FIG. 15 is a graph showing evaluation results of the in vitro BBB model in Example 15 ((A) and (B)). The error bar represents the standard deviation (n=3).
Figure 15:
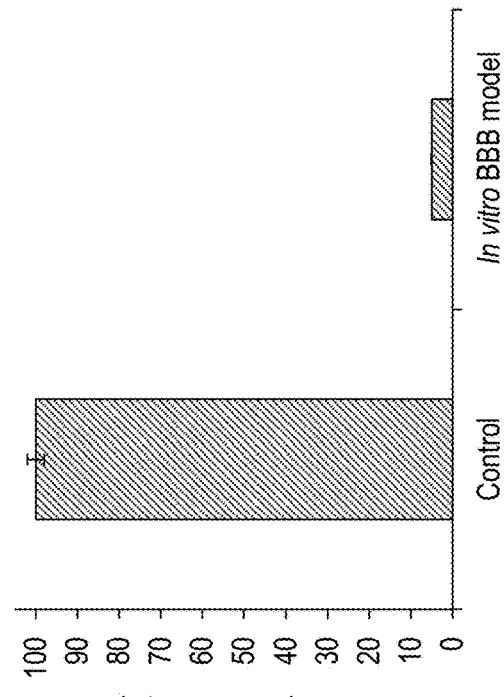

Results of the medium permeation assay are shown in FIG. 15A. The control showed that the medium completely passed through to a lower chamber, while the in vitro BBB model showed that the medium stayed in an upper chamber and the permeability of the medium was very low.

Next, the apical-to-basal permeability analysis was conducted by adding FITC-inulin with a low molecular weight (Sigma-Aldrich Co., LLC.), FITC-dextran 20 kDa with a medium molecular weight (Sigma-Aldrich Co., LLC.), or FITC-dextran 70 kDa with a high molecular weight (Sigma-Aldrich Co., LLC.) onto an upper chamber of an in vitro BBB model, and measuring fluorescence flowed into a lower chamber after 15 and 30 minutes. It was reported that inulin and dextran were used in an in vitro BBB model for testing drug permeability (Whilhelm, I., et al., Mol. Pharmaceutics, 2014, 11(7): 1949-1963). As a negative control, Transwell® a insert with no cells was utilized.

Results of the apical-to-basal permeability analysis are shown in FIG. 15B. In comparison with the control, the in vitro BBB model showed almost no permeability of inulin and dextran. After 30 minutes, a slight permeability of inulin with a low molecular weight was observed in the in vitro BBB model, which shows molecular weight-dependent permeation phenomenon, that is, lower molecular weight substances pass through more easily than higher molecular weight substances. This indicates that an in vitro BBB model functions in a similar manner to an in vivo blood brain barrier.

Further, the in vitro BBB model had a transendothelial electrical resistance (TEER) of 382 Ω/cm². If the TEER is greater than 300 Ω/cm², it is considered to well reflect in vivo conditions.

These results indicate that the in vitro BBB model produced in Example 14 well reflects an in vivo blood brain barrier.

Example 16

(Ability of Nanoparticles to Pass Through a Blood Brain Barrier)

Whether FITC-labeled curcin and nanoparticles produced in Production Examples 6 to 9 could pass through a blood brain barrier was investigated in the same manner as the apical-to-basal permeability analysis described in Example 15. FITC-labeled curcin was prepared by reacting purified curcin with FITC NHS ester (FITC-NHS, Dojindo) and separating the FITC-labeled curcin from free curcin and FITC by use of molecular cut-off technique. FITC-labeled curcin and nanoparticles produced in Production Examples 6 to 9 (concentration of 0.5 mg/ml) were added to an upper chamber of an in vitro BBB model produced in Example 14, and incubated for 4 hours. Thereafter, the fluorescence of FITC or quantum dots was measured and the permeability was evaluated.

Figure 16:
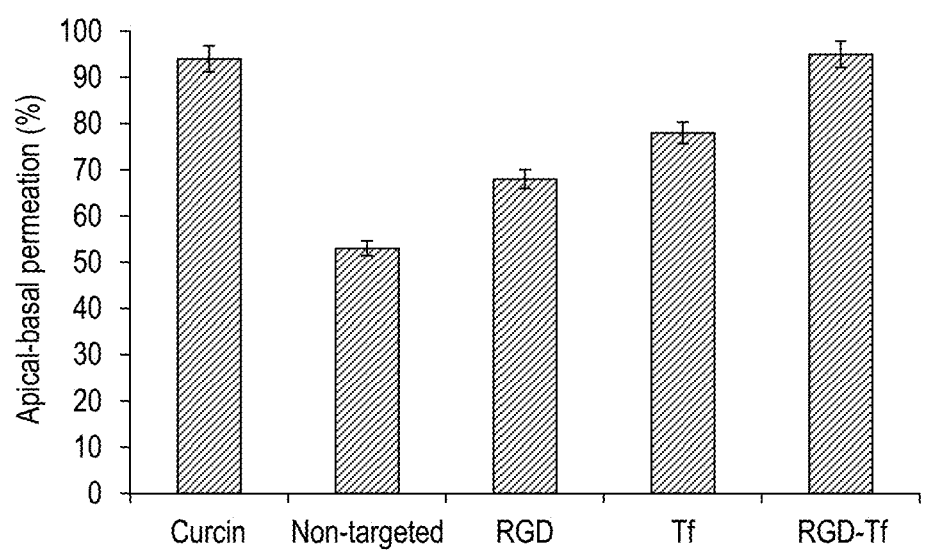
FIG. 16 is a graph showing results of the permeability analysis from the apical to the basal of each nanoparticle in Example 16. The error bar represents the standard deviation (n=3).

Results are shown in FIG. 16. Nanoparticles of Production Example 9 (RGD and transferrin-bound QD-nanoparticles) exhibited a high permeability of about 95%, followed by nanoparticles of Production Example 8 (transferrin-bound QD-nanoparticles) (82%) and nanoparticles of Production Example 7 (RGD-bound QD-nanoparticles) (70%). These results show that particularly RGD and transferrin-bound nanoparticles can effectively pass through a blood brain barrier.

Example 17

(Effect of Ratio of RGD and Transferrin on the Ability of Nanoparticles to Pass Through Blood Brain Barrier)

Nanoparticles having RGD tripeptide and transferrin bound thereto at different ratios were prepared. Nanoparticles (RGD2:Tf8) having RGD and transferrin bound thereto at a mass ratio of 2:8 (molar ratio of about 57:1) were prepared by the same method as in Production Example 9 except that activated RGD tripeptide corresponding to 0.4 mg of RGD tripeptide and activated transferrin corresponding to 1.6 mg of transferrin were used per 10 mg of nanoparticles. Nanoparticles (RGD4:Tf6) having RGD and transferrin bound thereto at a mass ratio of 4:6 (molar ratio of about 152:1) were prepared by the same method as in Production Example 9 except that activated RGD tripeptide corresponding to 0.8 mg of RGD tripeptide and activated transferrin corresponding to 1.2 mg of transferrin were used per 10 mg of nanoparticles. Nanoparticles (RGD6:Tf4) having RGD and transferrin bound thereto at a mass ratio of 6:4 (molecular ratio of about 342:1) were prepared by the same method as in Production Example 9 except that activated RGD tripeptide corresponding to 1.2 mg of RGD tripeptide and activated transferrin corresponding to 0.8 mg of transferrin were used per 10 mg of nanoparticles. Nanoparticles (RGD8:Tf2) having RGD and transferrin bound thereto at a mass ratio of 8:2 (molar ratio of about 913:1) were prepared by the same method as in Production Example 9 except that activated RGD tripeptide corresponding to 1.6 mg of RGD tripeptide and activated transferrin corresponding to 0.4 mg of transferrin per 10 mg of nanoparticles. Nanoparticles RGD2:Tf8, RGD4:Tf6, RGD6:Tf4 or RGD8:Tf2 (concentration of 0.5 mg/ml) were added to an upper chamber of an in vitro BBB model produced in Example 14 and were incubated for 4 hours. Thereafter, the fluorescence of quantum dots in a lower chamber was measured and the permeability was evaluated.

Figure 17:
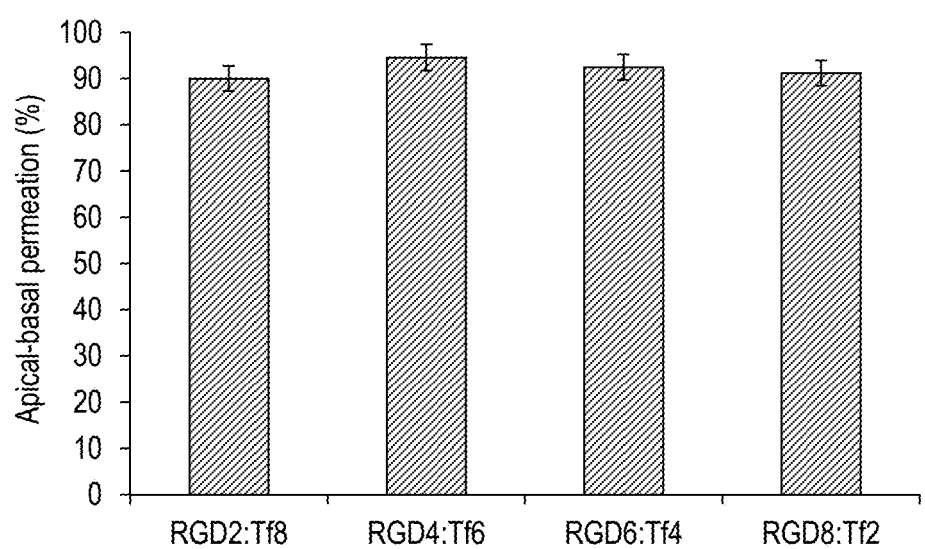
FIG. 17 is a graph showing results of the permeability analysis from the apical to the basal of each nanoparticle in Example 17. The error bar represents the standard deviation (n=3).

Results are shown in FIG. 17. All of the tested nanoparticles exhibited a high permeability of about 90% or more. In particular, RGD4:Tf6 exhibited the highest permeability of about 96%. These results show that nanoparticles having RGD tripeptide and transferrin at different ratios can efficiently pass through a blood brain barrier, and in particular, nanoparticles having RGD and transferrin at a mass ratio of 4:6 (molar ratio of about 152:1) can efficiently pass through a blood brain barrier.

Example 18

(Effect of the Type of Targeting Agent on the Ability of Nanoparticles to Pass Through Blood Brain Barrier)

Nanoparticles having different targeting agents alone or in combination, were prepared. In addition to the above-mentioned RGD tripeptide and transferrin, folic acid (FA) and Anginex were used as a targeting agent. Since folic acid binds to a folic acid receptor, which is overexpressed in many cancer cells such as glioblastoma, it targets cancer cells. Since Anginex binds to galectin-1, which is expressed in various tumors and endothelial cells, it targets tumor cells (cancer cells) and endothelial cells that form new blood vessels (angiogenesis).

1-ethyl-3-[3-dimenthylaminopropyl]carbodiimide hydrochloride (EDC) (Sigma-Aldrich Co., LLC.) and N-hydroxysuccinimide (NHS) (Sigma-Aldrich Co., LLC.) were added to 2 mg of folic acid (Sigma-Aldrich Co., LLC.), and reacted with each other overnight at 4° C. to activate folic acid. The activated folic acid was reacted overnight at 4° C. with 10 mg of nanoparticles of Production Example 6 (non-targeted QD-nanoparticles). The reaction solution was centrifuged at 50,000 rpm to pelletize the nanoparticles, thereby obtaining folic acid-bound nanoparticles.

EDC and NHS were added to 2 mg of Anginex (Phoenix Peptide), and reacted with each other overnight at 4° C. to activate Anginex. The activated Anginex was reacted overnight at 4° C. with 10 mg of nanoparticles of Production Example 6 (non-targeted QD-nanoparticles). The reaction solution was centrifuged at 50,000 rpm to pelletize the nanoparticles, thereby obtaining Anginex-bound nanoparticles.

Next, nanoparticles having two kinds of targeting agents were prepared. EDC and NHS were added to 2 mg of folic acid and reacted with each other overnight at 4° C. to activate folic acid. Anginex, RGD tripeptide and transferrin were each also activated in the same manner.

The activated folic acid (corresponding to 1 mg of folic acid) and the activated Anginex (corresponding to 1 mg of Anginex) were reacted with 10 mg of nanoparticles of Production Example 6 (non-targeted QD-nanoparticles) overnight at 4° C. The reaction solution was centrifuged at 50,000 rpm to pelletize the nanoparticles, thereby obtaining folic acid and Anginex-bound nanoparticles.

The activated folic acid (corresponding to 1 mg of folic acid) and the activated transferrin (corresponding to 1 mg of transferrin) were reacted with 10 mg of nanoparticles of Production Example 6 (non-targeted QD-nanoparticles)

overnight at 4° C. The reaction solution was centrifuged at 50,000 rpm to pelletize the nanoparticles, thereby obtaining folic acid and transferrin-bound nanoparticles.

The activated folic acid (corresponding to 1 mg of folic acid) and the activated RGD tripeptide (corresponding to 1 mg of RGD tripeptide) were reacted with 10 mg of nanoparticles of Production Example 6 (non-targeted QD-nanoparticles) overnight at 4° C. The reaction solution was centrifuged at 50,000 rpm to pelletize the nanoparticles, thereby obtaining folic acid and RGD tripeptide-bound nanoparticles.

The activated Anginex (corresponding to 1 mg of Anginex) and the activated transferrin (corresponding to 1 mg of transferrin) were reacted with 10 mg of nanoparticles of Production Example 6 (non-targeted QD-nanoparticles) overnight at 4° C. The reaction solution was centrifuged at 50,000 rpm to pelletize the nanoparticles, thereby obtaining Anginex and transferrin-bound nanoparticles.

The activated Anginex (corresponding to 1 mg of Anginex) and the activated RGD tripeptide (corresponding to 1 mg of RGD tripeptide) were reacted with 10 mg of nanoparticles of Production Example 6 (non-targeted QD-nanoparticles) overnight at 4° C. The reaction solution was centrifuged at 50,000 rpm to pelletized the nanoparticles, thereby obtaining Anginex and RGD tripeptide-bound nanoparticles.

The thus prepared nanoparticles and the nanoparticles of Production Examples 7 to 9 (concentration of 0.25 mg/ml) were added to an upper chamber of an in vitro BBB model produced in Example 14, and incubated for 4 hours. Thereafter, the fluorescence of quantum dots in a lower chamber was measured for evaluation of the permeability.

Figure 18:
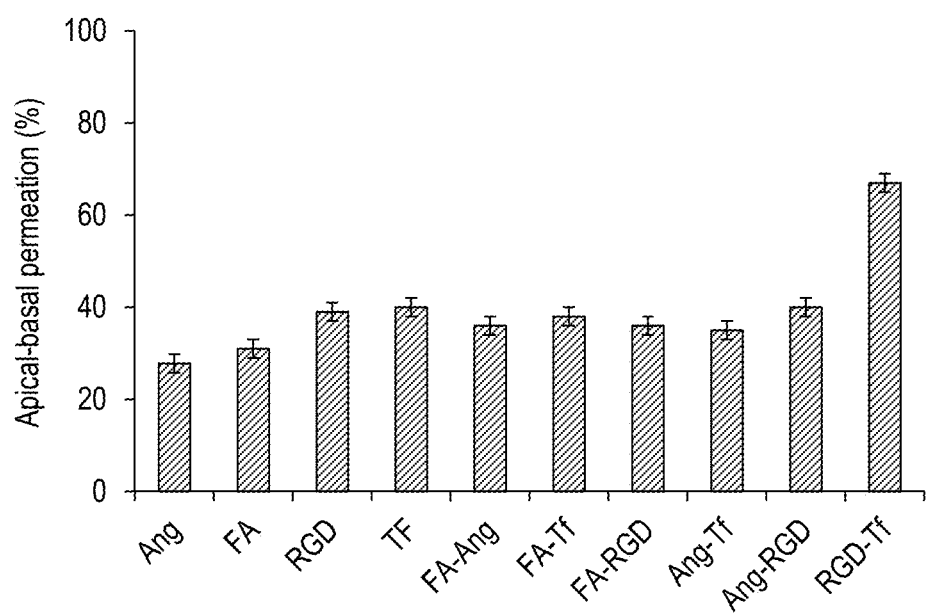
FIG. 18 is a graph showing results of the permeability analysis from the apical to the basal of each nanoparticle in Example 18. The error bar represents the standard deviation (n=3).

FIG. 18 shows results of the permeability of Anginex-bound nanoparticles (Ang), folic acid-bound nanoparticles (FA), RGD-bound QD-nanoparticles of Production Example 7 (RGD), transferrin-bound QD-nanoparticles of Production Example 8 (TO, folic acid and Anginex-bound nanoparticles (FA-Ang), folic acid and transferrin-bound nanoparticles (FA-TO, folic acid and RGD tripeptide-bound nanoparticles (FA-RGD), Anginex and transferrin-bound nanoparticles (Ang-Tf), Anginex and RGD tripeptide-bound nanoparticles (Ang-RGD), and RGD and transferrin-bound QD-nanoparticles of Production Example 9 (RGD-Tf). Nanoparticles having a combination of RGD tripeptide and transferrin exhibited the most excellent ability to pass through a blood brain barrier.

Example 19

(In Vitro Targeting to Glioblastoma)

G1-1 cells (RIKEN) were seeded on 12-well plates at a density of $1 \times 10^5$ cells/well and cultured for 24 hours. The cells were then treated for 2 hours with FITC-labelled curcin (described in Example 16), nanoparticles of Production Examples 6 to 9, nanoparticles having RGD tripeptide and transferrin bound at different ratios (described in Example 17), and nanoparticles having different targeting agents alone or in combination (described in Example 18). At the end of the treatment, the cells were washed with PBS three times and fixed with 4% paraformaldehyde, and the cellular uptake efficiency was analyzed by an FACS device (IntelliCyt).

Figure 19:
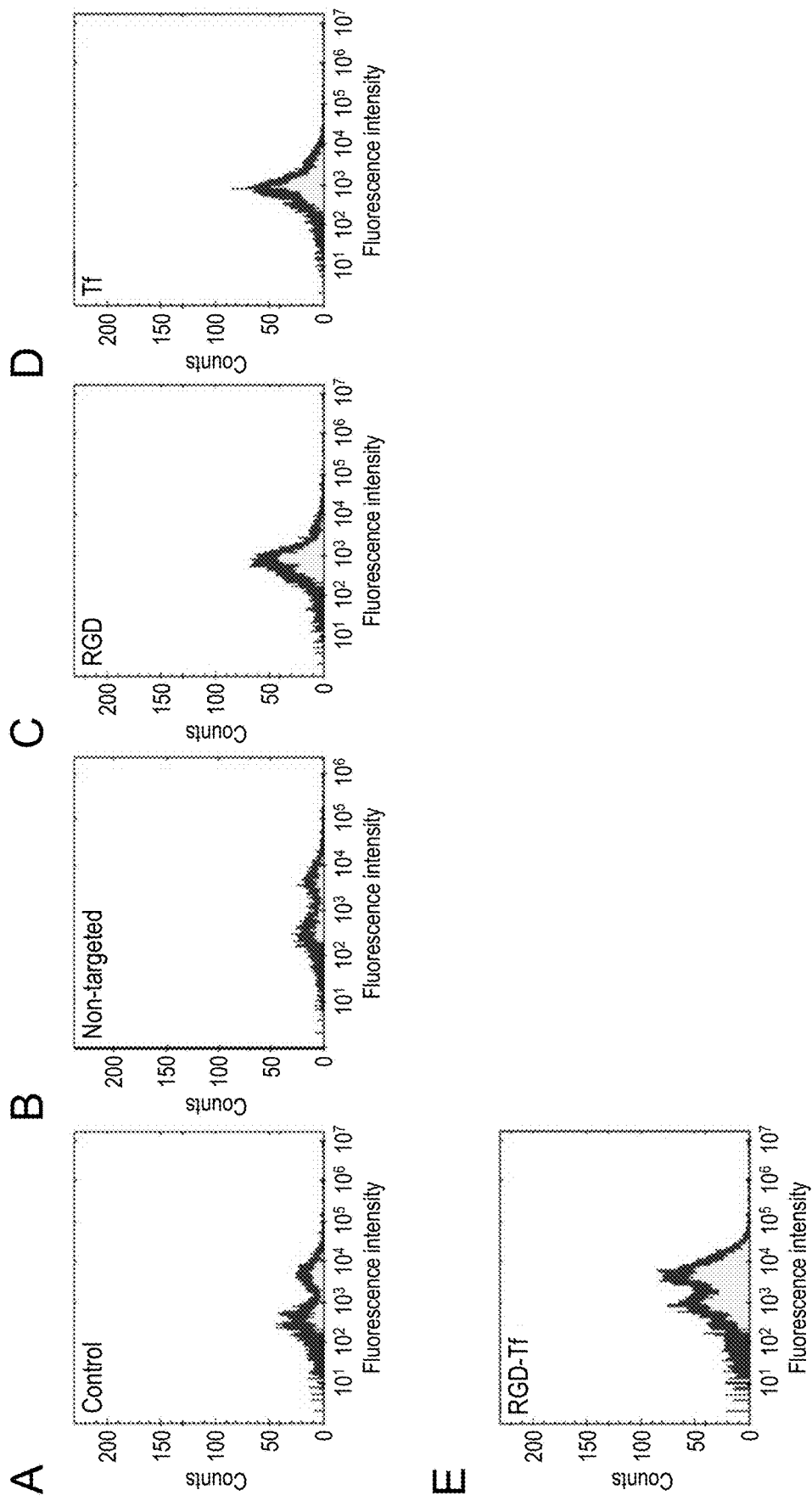
FIG. 19 is a graph showing analytical results using FACS device on targeting of each nanoparticle on glioblastoma cells in Example 19 ((A) to (E)).
Figure 20:
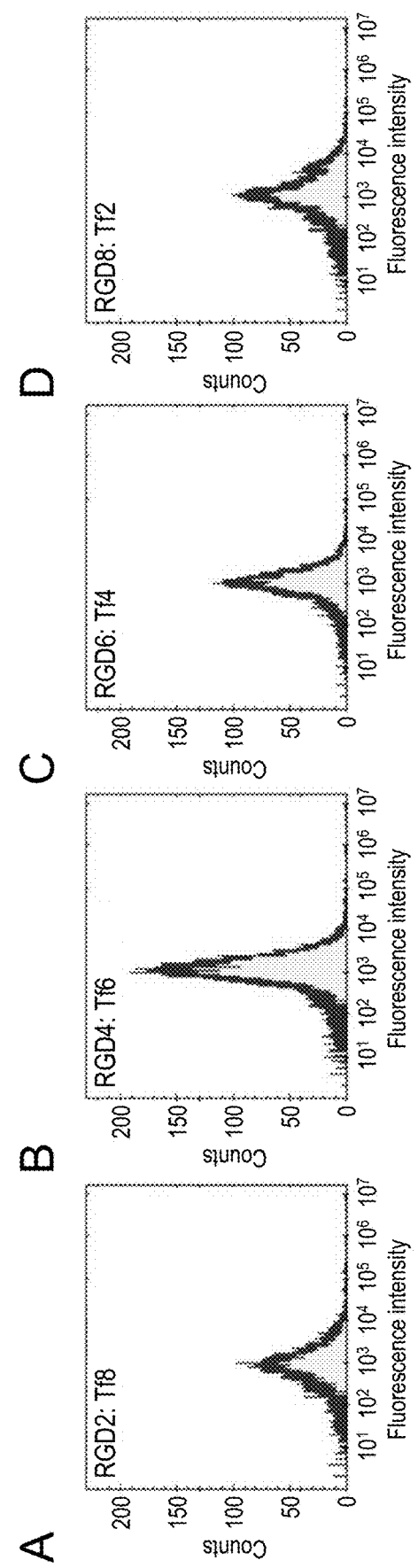
FIG. 20 is a graph showing analytical results using FACS device on targeting of each nanoparticle on glioblastoma cells in Example 19 ((A) to (D)).
Figure 21:
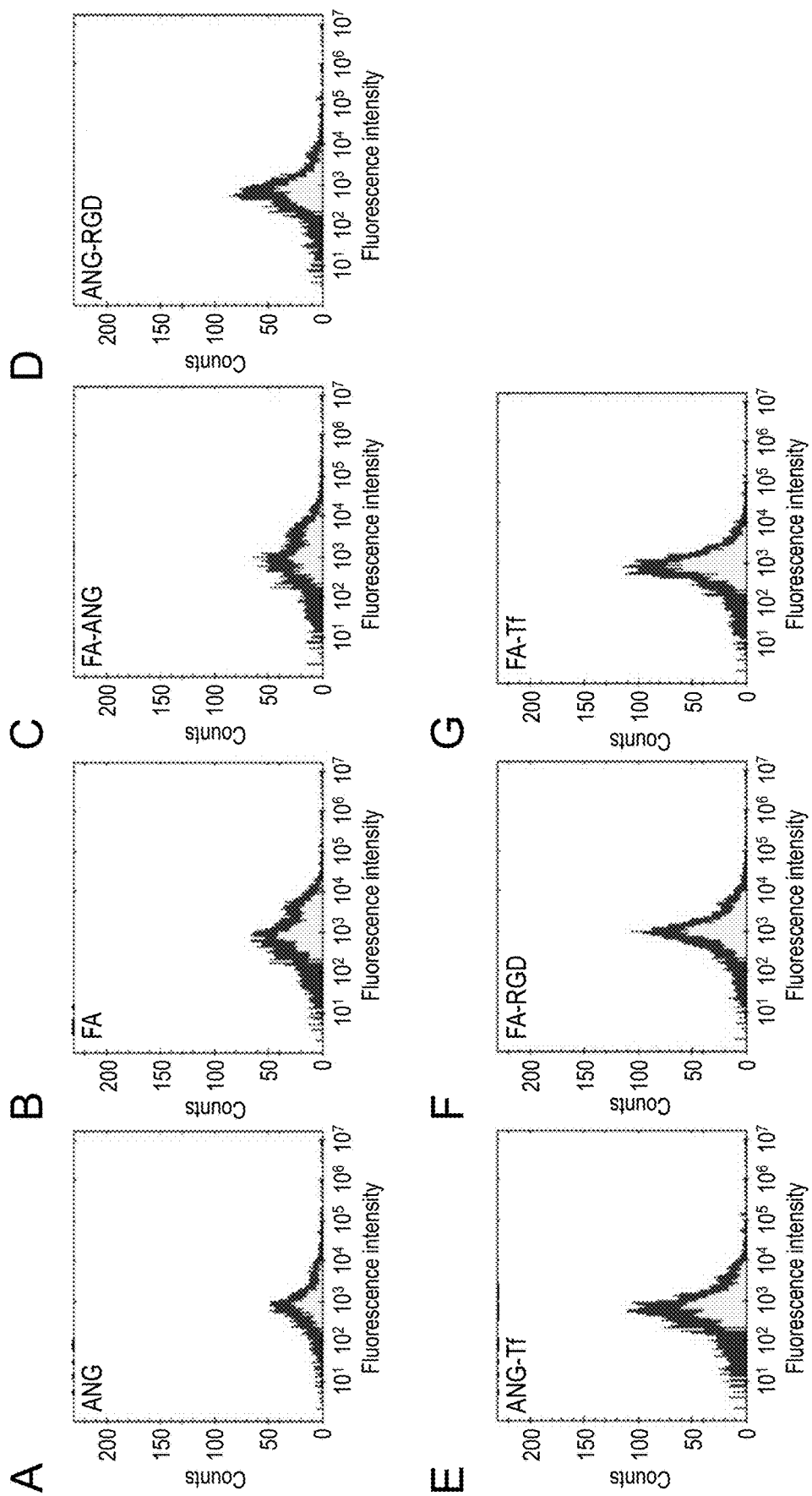
FIG. 21 is a graph showing analytical results using FACS device on targeting of each nanoparticle on glioblastoma cells in Example 19 ((A) to (G)).

Results are shown in FIGS. 19 to 21. These figures show analytical results: FIG. 19A for the control; FIG. 19B for nanoparticles of Production Example 6 (non-targeted QD-nanoparticles); FIG. 19C for nanoparticles of Production Example 7 (RGD-bound QD-nanoparticles); FIG. 19D for nanoparticles of Production Example 8 (transferrin-bound QD-nanoparticles); FIG. 19E for nanoparticles of Production Example 9 (RGD and transferrin-bound QD-nanoparticles); FIG. 20A for nanoparticle RGD2:Tf8; FIG. 20B for nanoparticle RGD4:Tf6; FIG. 20C for nanoparticle RGD6:Tf4; FIG. 20D for nanoparticle RGD8:Tf2; FIG. 21A for Anginex-bound nanoparticles; FIG. 21B for folic acid-bound nanoparticles; FIG. 21C for folic acid and Anginex-bound nanoparticles; FIG. 21D for Anginex and RGD tripeptide-bound nanoparticles; FIG. 21E for Anginex and transferrin-bound nanoparticles; FIG. 21F for folic acid and RGD tripeptide-bound nanoparticles; and FIG. 21G for folic acid and transferrin-bound nanoparticles.

Nanoparticles of Production Example 9 (RGD and transferrin-bound QD-nanoparticles) exhibited a higher accumulation (the intensity in the range of $10^3$ to $10^4$) in target cells compared with nanoparticles of Production Example 6 (non-targeted QD-nanoparticles), nanoparticles of Production Example 7 (RGD-bound QD-nanoparticles) and nanoparticles of Production Example 8 (transferrin-bound QD-nanoparticles) (FIGS. 19B to 19E), and this has showed an excellent targeting efficiency of the RGD and transferrin-bound nanoparticles. When the ratio between RGD tripeptide and transferrin varied, the RGD:transferrin mass ratio of 4:6 has exhibited the highest accumulation in glioblastoma cells (FIGS. 20A to 20D). Further, various targeting agents and their combinations were tested (FIG. 21A to 21G), but nothing exhibited a more excellent accumulation than the combination of RGD and transferrin. These results showed that, in particular, nanoparticles having RGD and transferrin in combination are capable of efficiently targeting and accessing glioblastoma cells as target cells.

Example 20

(Loading and Release of a Further Drug)

Nanoparticles comprising doxorubicin or paclitaxel as a drug were prepared and used for examination of loading and release of the drug.

Nanoparticles were prepared by a modified method of lipid coacervation. Equal concentrations of 1,2-distearoyl-sn-glycero-3-phosphoethanolamine-N-[amino(polyethyleneglycol)-2000] (DSPE-PEG(2000) Amine, Avanti Polar Lipids, Inc.), stearic acid (Sigma-Aldrich Co., LLC.) and lecithin (Sigma-Aldrich Co., LLC.) were dissolved in chloroform and desiccated overnight to form a thin film.

Then, the thin film was hydrated with a solution of a drug of doxorubicin (DOX, Sigma-Aldrich Co., LLC.) or paclitaxel (PTX, Wako Pure Chemical Industries, Ltd.) in a buffer and sonicated for several minutes, thereby obtaining a transparent and stable suspension. Subsequently, the suspension was centrifuged at 50,000 rpm for 30 minutes by a centrifuge (Hitachi) to pelletize drug-loaded nanoparticles (washing process). This washing process was repeated, thereby obtaining drug-loaded nanoparticles. Doxorubicin is an anti-cancer agent of an anthracycline compound, which is a hydrophilic compound with a molecular weight of about 544. Paclitaxel is an anti-cancer agent of a taxane compound, which is a hydrophobic compound with a molecular weight of about 854.

Figure 22:
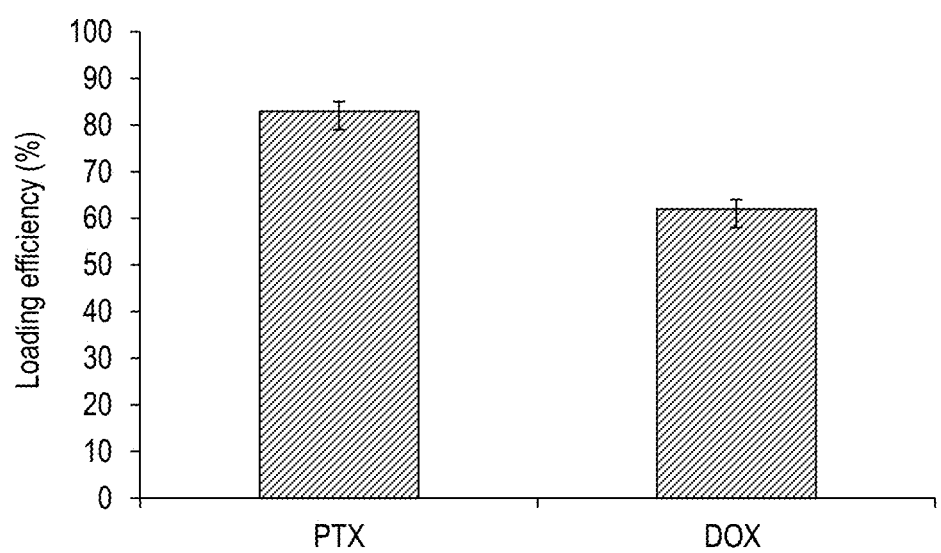
FIG. 22 is a graph showing loading efficiencies of a further drug in Example 20. The error bar represents the standard deviation (n=3).

Lipid shells of nanoparticles were lysed with 10% Triton X, and the drug-loading efficiency of nanoparticles was quantified. The absorbance of released drugs (at 450 nm for doxorubicin and at 280 nm for paclitaxel) was read by use of a spectrophotometer (model of "UV-2100PC/3100PC", Shimadzu Corporation). Previously created standard curves indicating the relationship between the drug concentration and the absorbance were used to convert a measured absorbance into a drug concentration. The drug loading efficiency (%) was calculated as a ratio of the amount of a drug (drug loaded on nanoparticles) released by lysis of the above lipid shell relative to the total amount of drugs used for preparation of drug-loaded nanoparticles. The drug-loading efficiencies are shown in FIG. 22. The loading efficiencies of doxorubicin and paclitaxel on nanoparticles were shown to be about 83% and about 62%, respectively.

Figure 23:
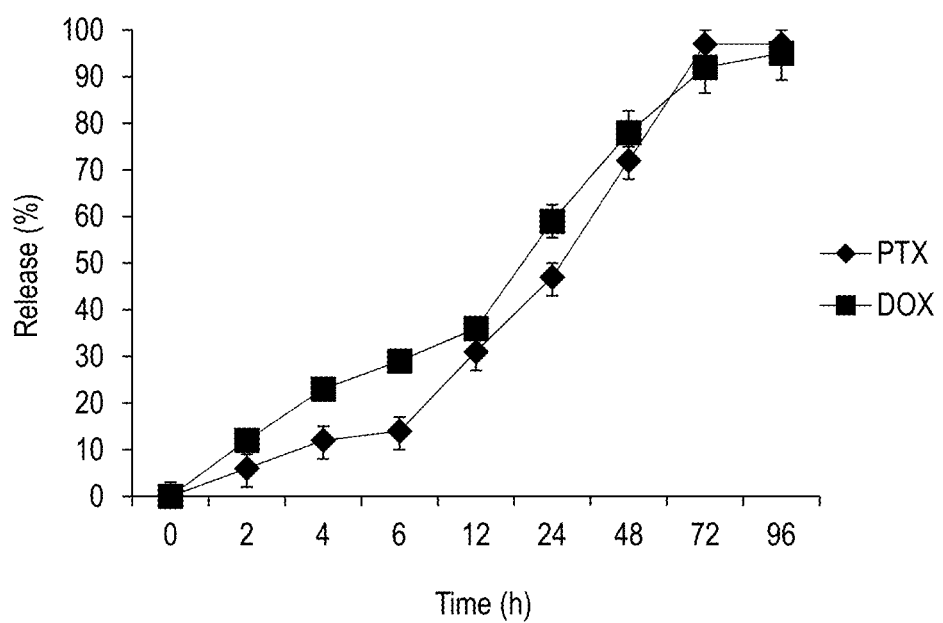
FIG. 23 is a graph showing release profiles of a further drug in Example 20. The error bar represents the standard deviation (n=3).

Next, drug-loaded nanoparticles were incubated in PBS with a physiological pH (7.2) for different time periods (0 to 96 hours) and then, pelletized by centrifugation; and the absorbance of a supernatant containing released drugs was read by use of a spectrophotometer (model of "UV-2100PC/3100PC", Shimadzu Corporation). Previously created standard curves indicating the relationship between the drug concentration and the absorbance were used to convert a measured absorbance into a drug concentration. The release ratio (%) was calculated as a ratio of released drugs to drugs loaded on nanoparticles. Drug release profiles are shown in FIG. 23. The release of drugs was kept at a high level for a long period. The release of doxorubicin from nanoparticles was 29% (at 6 hours), 59% (at 24 hours) and 92% (at 72 hours). The release profile of paclitaxel was similar to that of doxorubicin. These results show that drugs were released from nanoparticles in a gentle and continuous manner.

INDUSTRIAL APPLICABILITY

The present invention can provide a nanoparticle composition having low cytotoxicity, which can be utilized for a drug delivery system, etc. that passes through a blood brain barrier.

All publications, patents and patent applications cited in this specification are incorporated herein by reference in their entirety.

The invention claimed is:

1. A nanoparticle composition comprising nanoparticles to the surface of which a first substance and a second substance each having specificity to a tumor cell are bound, wherein the first substance having specificity to the tumor cell is a peptide comprising an amino acid sequence of arginine-glycine-aspartic acid,
wherein the second substance having specificity to the tumor cell is transferrin,
wherein the nanoparticle composition comprises the first substance and the second substance at a mass ratio of 2:8 to 8:2, and
wherein the nanoparticles each comprise an outer layer and vesicles enveloped by the outer layer, and the nanoparticles comprise membrane components that comprising a PEGylated phospholipid, stearic acid, and phosphatidylcholine,
wherein the PEGylated phospholipid is phosphatidylethanolamine to which PEG is bound and the PEG is modified with the amino group.

2. The nanoparticle composition according to claim 1, wherein the phosphatidylethanolamine is DSPE.

3. The nanoparticle composition according to claim 1, wherein the nanoparticle further comprises a drug.

4. The nanoparticle composition according to claim 3, wherein the drug is an anti-cancer agent.

5. The nanoparticle composition according to claim 1, wherein the nanoparticle further comprises an imaging agent.

6. A method for producing the nanoparticle composition comprising nanoparticles to the surface of which a first substance and a second substance each having specificity to a tumor cell are bound according to claim 1, comprising:
(i) removing a volatile organic solvent from a solution comprising a PEGylated phospholipid, stearic acid, and phosphatidylcholine in the volatile organic solvent to form a membrane,
wherein the PEGylated phospholipid is phosphatidylethanolamine to which PEG is bound and the PEG is modified with an amino group,
(ii) sonicating the membrane formed in the step (i) in a buffer to produce nanoparticles, and (iii) binding the first substance and the second substance each having specificity to the tumor cell to the surface of the nanoparticles produced in the step (ii) at a mass ratio of 2:8 to 8:2, wherein the first substance having specificity to the tumor cell is a peptide comprising an amino acid sequence of arginine-glycine-aspartic acid, and wherein the second substance having specificity to the tumor cell is transferrin.

7. The method according to claim 6, wherein in the step (ii), the buffer comprises a drug, and nanoparticles comprising the drug are produced.

8. The method according to claim 7, wherein the drug is an anti-cancer agent.

9. The method according to claim 6, further comprising introducing an imaging agent into the nanoparticle.

10. A pharmaceutical composition for treating cancer, comprising the nanoparticle composition according to claim 4.

11. The pharmaceutical composition according to claim 10, wherein the cancer is a brain tumor.

12. A composition for imaging a tumor cell, comprising the nanoparticle composition according to claim 5.

13. A method for detecting a brain tumor, comprising administering the composition according to claim 5 to a subject in need thereof and detecting a localization of the imaging agent in a brain.

14. A method for monitoring the effect of a therapy against a brain tumor, comprising administering the composition according to claim 5 to a subject in need thereof and detecting a localization of the imaging agent in a brain.

15. The nanoparticle composition according to claim 1, wherein the nanoparticles are produced by (i) removing a volatile organic solvent from a solution comprising the PEGylated phospholipid, stearic acid, and phosphatidylcholine in the volatile organic solvent to form a membrane, (ii) sonicating the membrane formed in the step (i) in a buffer to produce nanoparticles, and (iii) binding said first substance and said second substance each having specificity to the tumor cell to the surface of the nanoparticles produced in the step (ii) at a mass ratio of 2:8 to 8:2.

16. The nanoparticle composition according to claim 15, wherein the sonicating in the step (ii) is carried out at 43 kHz for 1 to 2 minutes.

17. The method according to claim 6, wherein the sonicating in the step (ii) is carried out at 43 kHz for 1 to 2 minutes.

\* \* \* \* \*

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: RGD peptide

<400> SEQUENCE: 1

Gly Arg Gly Asp Ser
1               5

<210> SEQ ID NO 2
<211> LENGTH: 6
<212> TYPE: PRT
<213> ORGANISM: Artificial Sequence
<220> FEATURE:
<223> OTHER INFORMATION: RGD peptide

<400> SEQUENCE: 2

Gly Arg Gly Asp Asn Pro
1               5
```